United States Patent
Malik et al.

(10) Patent No.: US 10,604,628 B2
(45) Date of Patent: *Mar. 31, 2020

(54) POLYMER AND THERMOSETTING COMPOSITION CONTAINING SAME

(71) Applicant: Fujifilm Electronic Materials U.S.A., Inc., N. Kingstown, RI (US)

(72) Inventors: Sanjay Malik, Attleboro, MA (US); William A. Reinerth, Riverside, RI (US); Binod B. De, Attleboro, MA (US); Ahmad A. Naiini, East Greenwich, RI (US)

(73) Assignee: Fujifilm Electronic Materials U.S.A., Inc., N. Kingstown, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/608,410

(22) Filed: May 30, 2017

(65) Prior Publication Data

US 2017/0260330 A1 Sep. 14, 2017

Related U.S. Application Data

(63) Continuation of application No. 14/279,553, filed on May 16, 2014, now Pat. No. 9,695,284.

(60) Provisional application No. 61/824,529, filed on May 17, 2013.

(51) Int. Cl.

| | | |
|---|---|---|
| C08G 73/10 | (2006.01) | |
| C09D 179/08 | (2006.01) | |
| C08K 5/1535 | (2006.01) | |
| C08K 5/101 | (2006.01) | |
| C08K 5/06 | (2006.01) | |
| C08K 5/07 | (2006.01) | |
| C08J 5/18 | (2006.01) | |
| H01L 21/02 | (2006.01) | |
| H01L 23/29 | (2006.01) | |
| B05D 1/00 | (2006.01) | |
| B05D 1/02 | (2006.01) | |
| C07C 211/09 | (2006.01) | |
| C07C 321/00 | (2006.01) | |
| C08K 5/00 | (2006.01) | |

(52) U.S. Cl.
CPC ......... *C08G 73/1032* (2013.01); *B05D 1/005* (2013.01); *B05D 1/02* (2013.01); *C07C 211/09* (2013.01); *C07C 321/00* (2013.01); *C08G 73/1014* (2013.01); *C08G 73/1039* (2013.01); *C08G 73/1042* (2013.01); *C08G 73/1067* (2013.01); *C08G 73/1071* (2013.01); *C08J 5/18* (2013.01); *C08K 5/0025* (2013.01); *C08K 5/06* (2013.01); *C08K 5/07* (2013.01); *C08K 5/101* (2013.01); *C08K 5/1535* (2013.01); *C09D 179/08* (2013.01); *H01L 21/02118* (2013.01); *H01L 21/02282* (2013.01); *H01L 23/293* (2013.01); *C07C 2602/08* (2017.05); *C08J 2379/08* (2013.01)

(58) Field of Classification Search
CPC .. C08G 73/10; C08G 73/101; C08G 73/1014; C08K 5/0025; C08K 5/37
USPC ......................................................... 524/600
See application file for complete search history.

(56) References Cited

U.S. PATENT DOCUMENTS

| | | |
|---|---|---|
| 3,856,752 A | 12/1974 | Bateman et al. |
| 3,983,092 A | 9/1976 | Bateman et al. |
| 3,993,630 A | 11/1976 | Darmory et al. |
| 4,122,076 A | 10/1978 | Jablonski et al. |
| 4,558,117 A | 12/1985 | Nakano et al. |
| 4,684,714 A | 8/1987 | Lubowitz et al. |
| 4,689,378 A | 8/1987 | Chaudhari et al. |
| 4,734,482 A | 3/1988 | Tamai et al. |
| 4,775,734 A | 10/1988 | Goel |
| 4,923,954 A | 5/1990 | Klobucar et al. |
| 5,025,084 A | 6/1991 | Dobinson et al. |
| 5,047,487 A | 9/1991 | Camargo et al. |
| 5,397,847 A | 3/1995 | Harris et al. |
| 5,412,065 A | 5/1995 | Amone et al. |
| 5,478,915 A | 12/1995 | Amone et al. |
| 5,606,013 A | 2/1997 | Chaudhari et al. |
| 5,618,655 A | 4/1997 | Davidson |
| 5,637,772 A | 6/1997 | Malik et al. |
| 5,643,998 A | 7/1997 | Nakano et al. |
| 5,914,385 A | 6/1999 | Hayashi et al. |
| 5,945,251 A | 8/1999 | Davidson |
| 6,303,744 B1 | 10/2001 | Meador et al. |
| 7,312,281 B2 | 12/2007 | Sheehan et al. |
| 8,039,579 B2 | 10/2011 | McManus et al. |
| 2002/0182536 A1 | 12/2002 | Kamada et al. |
| 2004/0235992 A1 | 11/2004 | Okada et al. |
| 2006/0083928 A1 | 4/2006 | Miyagawa et al. |
| 2007/0269665 A1 | 11/2007 | Shimoohsako et al. |

(Continued)

FOREIGN PATENT DOCUMENTS

| | | | |
|---|---|---|---|
| CN | 1366534 | 8/2002 | ............ C08G 73/10 |
| CN | 103289090 | 9/2013 | |

(Continued)

OTHER PUBLICATIONS

Chinese Office Action for Chinese Application No. 201480028805.5 dated Jun. 27, 2017, and its English translation.

(Continued)

Primary Examiner — Jane L Stanley
(74) Attorney, Agent, or Firm — Fish & Richardson P.C.

(57) ABSTRACT

This disclosure relates to a polymer that includes a first repeat unit and at least one end-cap group at one end of the polymer. The first repeat unit includes at least one imide moiety and at least one indane-containing moiety. The end-cap group is capable of undergoing a cycloreversion reaction. This disclosure also relates to a thermosetting composition containing the above polymer.

39 Claims, No Drawings

(56) References Cited

U.S. PATENT DOCUMENTS

| | | | |
|---|---|---|---|
| 2009/0069508 A1 | 3/2009 | Poe et al. | |
| 2009/0253805 A1 | 10/2009 | Hoyle et al. | |
| 2009/0306329 A1 | 12/2009 | Hasegawa | |
| 2013/0059985 A1 | 3/2013 | Kutsuzawa | |

FOREIGN PATENT DOCUMENTS

| | | | |
|---|---|---|---|
| EP | 0 317 754 | 5/1989 | |
| EP | 0 531 259 | 3/1993 | ............ C08G 73/10 |
| EP | 0 626 412 | 11/1994 | |
| FR | 2 609 037 | 7/1988 | |
| JP | 57-108158 | 7/1982 | |
| JP | 61-254543 | 11/1986 | |
| JP | S62-29584 | 2/1987 | ............ C07D 207/00 |
| JP | H5-331287 | 12/1993 | ............ C08G 73/10 |
| JP | H6-329794 | 11/1994 | ............ C08G 73/10 |
| JP | 2008/081713 | 4/2008 | |
| JP | 2008-222858 | 9/2008 | ............ C08G 73/10 |
| JP | 2013-006958 | 1/2013 | ............ C10B 57/04 |
| TW | 201200542 | 1/2012 | |
| WO | WO 99/58579 | 11/1999 | |
| WO | WO 2010/111755 | 10/2010 | |
| WO | WO 2012/007499 | 1/2012 | |
| WO | WO 2014/111998 | 7/2014 | ............ C08G 73/10 |

OTHER PUBLICATIONS

Taiwan Official Letter and Search Report for Taiwan Application No. TW 103117301 dated Aug. 1, 2017 and English summary (8 pages).

International Search Report and Written Opinion for International Application No. PCT/US14/38424 dated Sep. 19, 2014 (12 pages).

Supplementary European Search Report for European Application Serial No. EP 14 79 7717 dated Dec. 23, 2016.

Alston, et al., "Cyclopentadiene Evolution During Pyrolysis-Gas Chromatography of PMR Polyimides", *NASA Technical Memorandum* 105629, Technical Report 91-C-023, Prepared for the Fourth International Conference of Polyimides, Ellenville, NY, (Oct. 30-Nov. 1, 1991).

Meador, et al., "Oxidative Degradation of Nadic-End-Capped Polyimides. 2. Evidence for Reactions Occurring at High Temperatures", *Macromolecules,* vol. 30, No. 11, pp. 3215-3223 (1997).

Notification of Reasons for Refusal from the Japanese Patent Office for Japanese Application No. 2016-514133, dated Aug. 20, 2018 (With English Translation).

Japanese Office Action for Japanese Patent Application No. JP 2016-514154 dated Sep. 18, 2018.

Mahmoud et al., "Renewable productin of phthalic anhydride from biomass-derived furan and maleic anhydride", *Green Chemistry,* The Royal Society of Chemistry, vol. 16, pp. 167-175 (2014).

POLYMER AND THERMOSETTING COMPOSITION CONTAINING SAME

CROSS-REFERENCE TO RELATED APPLICATIONS

The present application is a continuation of and claims priority to U.S. application Ser. No. 14/279,553, filed on May 16, 2014, which claims priority to U.S. Provisional Application Ser. No. 61/824,529, filed on May 17, 2013. The contents of the prior applications are hereby incorporated by reference in its entirety.

FIELD OF THE DISCLOSURE

The present disclosure relates to low temperature cure, highly organic solvent soluble polyimide polymers and thermosetting compositions containing said polymers. More particularly, the disclosure relates to thermosetting compositions comprising said polymers and multifunctional thiols and processes for producing a substrate coated with a cured, thermoset film from the thermosetting compositions comprising said polymers and multifunctional thiols. Compositions of the disclosure have extensive use as thermoset coatings, particularly in the electronics industry, for example, as heat resist coatings, insulation coatings, dielectric films, barrier coatings, and encapsulants. Such coatings may be deposited by a variety of processes, but are particularly advantageous for coatings produced using inkjet technology.

BACKGROUND OF THE DISCLOSURE

Polyimides are widely used in the manufacture of electronic components as a film-forming resin possessing excellent electrical, mechanical, chemical and thermal characteristics. Each particular use has its particular physical and chemical requirements. However, in many cases the polyimide required for the application has limited or no solubility in the solvents acceptable for applying the polyimide films. Numerous highly polar solvents are not acceptable for film casting due to safety or boiling point issues, so solubility in moderate polarity solvents is required. As a result, many of the coatings are cast as the somewhat more solvent soluble polyamic acid film and then cured at high temperatures. This may result in some damage to the substrate/device and the equipment employed in the high temperature cure. Furthermore, the dehydration of the polyamic acid to polyimide shrinks the film by approximately 15-20%, which frequently increases the stress on the film, and thus the underlying substrate/device.

The growth of Inkjet technology for various coating applications has been strong. Particular advantages include the lowering the amount of coating solution required, and the ability to coat in specific areas, which can reduce the need for lithographic patterning steps. However, in order to reproducibly manufacture semiconductor devices, certain requirements must be met, such as excellent patternability, storage stability, minimal number of applications to obtain desired film thickness, low tendency to clog the tiny inkjet nozzles even with long delays between jetting uses, compatibility with the inkjet head, and uniform droplet formation. Prior art polyamic acids and polyimides tend to have low solubility in common inkjet solvents, which results in poor drop formation, inferior storage stability, and significant clogging of the inkjet nozzles.

Thus, there is a need for thermosetting compositions employing polyimide polymers highly soluble in moderate polarity solvents for various applications. The present disclosure describes a highly soluble class of polyimide polymers and their novel thermosetting compositions suitable for use in microelectronic applications. Compositions of the present disclosure are particularly suitable for deposition using inkjet printing due to their high solubility, excellent storage stability, and low clogging of inkjet nozzles.

BRIEF SUMMARY OF THE DISCLOSURE

In one aspect, the present disclosure features a polymer that includes a first repeat unit and at least one end-cap group at one end of the polymer. The first repeat unit includes at least one polyimide moiety and at least one indane-containing moiety. The end-cap group is capable of undergoing a cycloreversion reaction (e.g., in the solid state at a temperature at most about 250° C.).

In another aspect, the present disclosure features a polymer that includes the condensation product of: (a) at least one diamine; (b) at least one dianhydride; and (c) at least one monoanhydride comprising a group capable of undergoing a cycloreversion reaction (e.g., in the solid state at a temperature at most about 250° C.). At least one of components (a) and (b) includes an indane-containing moiety. The polymer contains at least one end-cap group at one end, the end-cap group containing the group capable of undergoing a cycloreversion reaction.

In some embodiments, the polymer described above can be a polyimide, a polyamic acid, or a copolymer thereof.

In some embodiments, the monoanhydride includes a masked maleic anhydride group. For example, the monoanhydride is of Structure (IX):

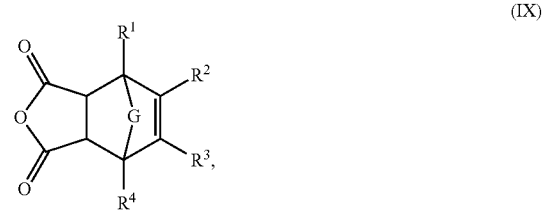

(IX)

in which G is —O—, —(NR$^{100}$)—, —[C(R$^{101}$)=C(R$^{102}$)]—, or —[C=C(R$^{103}$)$_2$]—, where each of R$^{100}$, R$^{101}$, R$^{102}$, and R$^{103}$, independently, is H, a substituted or unsubstituted C$_1$-C$_{12}$ linear or branched, monocyclic or polycyclic alkyl group, or a substituted or unsubstituted phenyl group, and each of R$^1$, R$^2$, R$^3$ and R$^4$, independently, is H, a substituted or unsubstituted C$_1$-C$_{12}$ linear or branched, monocyclic or polycyclic alkyl group, a substituted or unsubstituted phenyl group, OR$^{104}$, CH$_2$OR$^{105}$, CH$_2$OC(=O)R$^{106}$, CH$_2$C(=O)OR$^{107}$, CH$_2$NHR$^{108}$, CH$_2$NHC(=O)R$^{109}$, CH$_2$C(=O)N(R$^{110}$)$_2$, C(=O)OR$^{111}$, where each of R$^{104}$, R$^{105}$, R$^{106}$, R$^{107}$, R$^{108}$, R$^{109}$, R$^{110}$, and R$^{111}$, independently, is H or a substituted or unsubstituted C$_1$-C$_6$ linear, branched, or monocyclic alkyl group.

In some embodiments, the end-cap group includes a masked maleimide group. For example, the end-cap group can include a moiety of Structure (IXa):

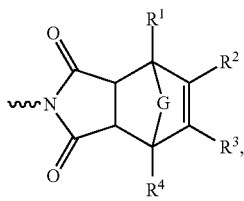
(IXa)

in which G is —O—, —(NR$^{100}$)—, —[C(R$^{101}$)=C(R$^{102}$)]—, or —[C=C(R$^{103}$)$_2$]—, where each of R$^{100}$, R$^{101}$, R$^{102}$, and R$^{103}$, independently, is H, a substituted or unsubstituted C$_1$-C$_{12}$ linear, branched, monocyclic or polycyclic alkyl group, or a substituted or unsubstituted phenyl group, and each of R$^1$, R$^2$, R$^3$ and R$^4$, independently, is H, a substituted or unsubstituted C$_1$-C$_{12}$ linear, branched, monocyclic or polycyclic alkyl group, a substituted or unsubstituted phenyl group, OR$^{104}$, CH$_2$OR$^{105}$, CH$_2$OC(=O)R$^{106}$, CH$_2$C(=O)OR$^{107}$, CH$_2$NHR$^{108}$, CH$_2$NHC(=O)R$^{109}$, CH$_2$C(=O)N(R$^{110}$)$_2$, C(=O)OR$^{111}$, where each of R$^{104}$, R$^{105}$, R$^{106}$, R$^{107}$, R$^{108}$, R$^{109}$, R$^{110}$, and R$^{111}$, independently, is H, or a substituted or unsubstituted C$_1$-C$_6$ linear, branched, or monocyclic alkyl group.

In some embodiments, the indane-containing moiety includes

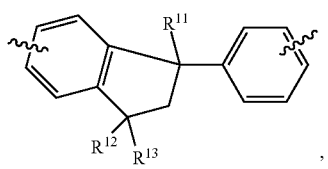

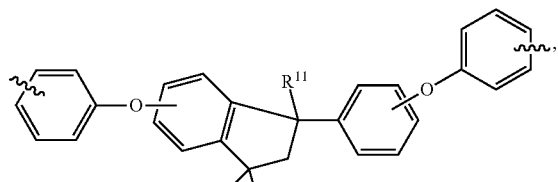

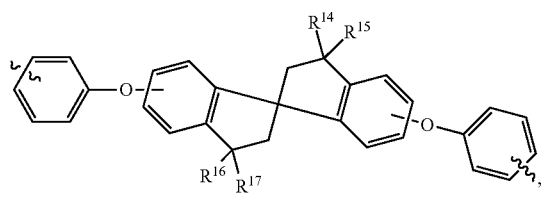

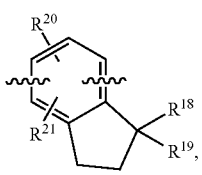

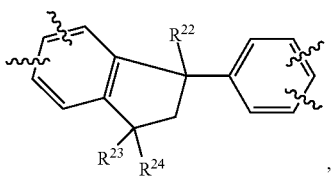

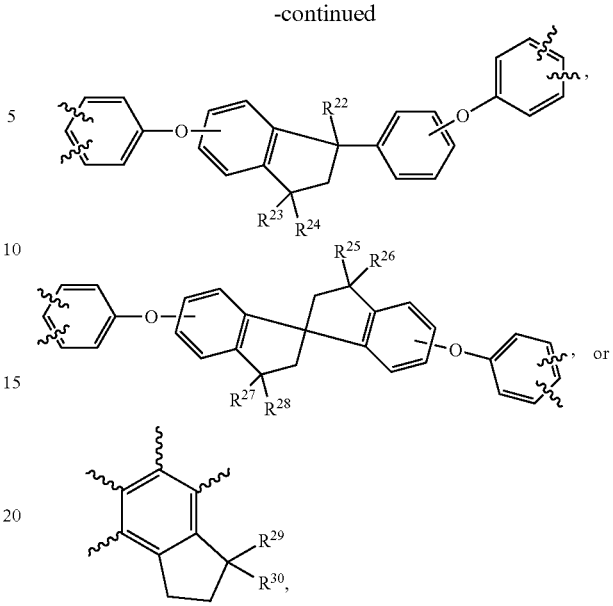

in which each of R$^{11}$-R$^{30}$, independently, is H or a substituted or unsubstituted C$_1$-C$_{10}$ linear or branched alkyl group (e.g., CH$_3$).

In some embodiments, the polymer can further include a second repeat unit different from the first repeat unit.

In some embodiments, the component containing the indane-containing moiety is at least about 25 mole % of components (a) and (b).

In another aspect, the present disclosure is directed to end-capped polyimide polymers of Structure I.

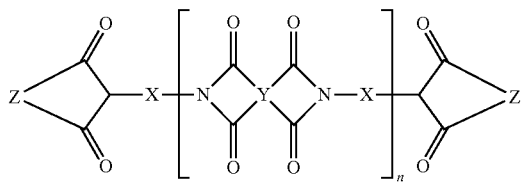
Structure I where Z is a divalent organic group capable of undergoing a cycloreversion reaction (e.g., in the solid state at a temperature at most about 250° C.), n is an integer greater than 5, X is a divalent organic group selected from one or more of the group of X$^1$ and X$^2$ where X$^1$ is one or more of the structures X$^{1a}$-X$^{1d}$ where R$^{11}$ to R$^{21}$ are independently H, a substituted or unsubstituted C$_1$-C$_{10}$ linear or branched alkyl group (e.g., a partially or fully halogen substituted C$_1$-C$_{10}$ alkyl group):

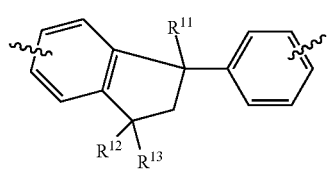
X$^{1a}$

-continued

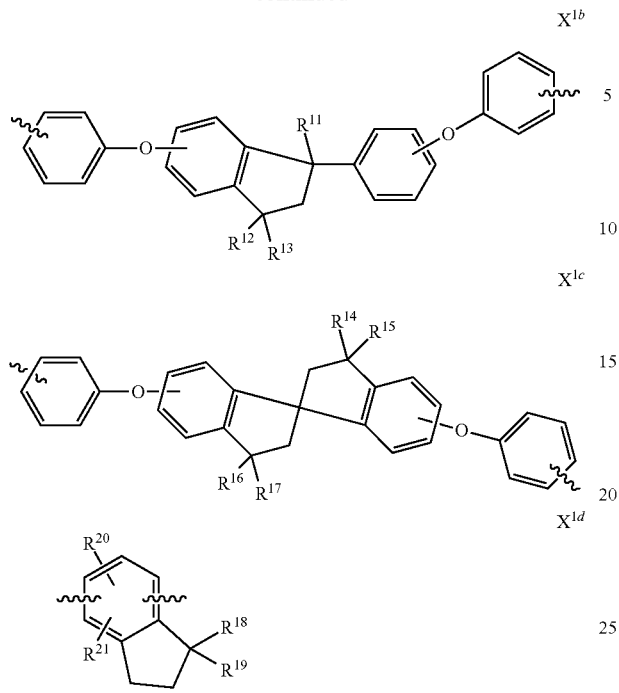

and X² is a divalent organic group selected from the group consisting of
- a) a substituted or unsubstituted $C_6$-$C_{18}$ mononuclear or polynuclear aromatic group,
- b) a substituted or unsubstituted $C_1$-$C_{20}$ linear, branched, monocyclic or polycyclic alkylene group,
- c) a substituted or unsubstituted heterocyclic radical,
- d) a linear or branched alkylene group containing one or more oxygen atoms, sulfur atoms, or $NR^{91}$ groups within the chain, in which $R^{91}$ is a $C_1$-$C_3$ alkyl group,
- e) a divalent group of Structure $IV^a$, $IV^b$, or $IV^c$,

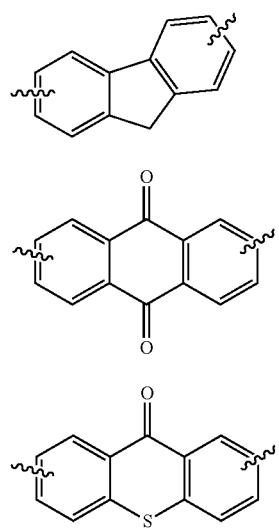

- f) a divalent group $[A^1-(B^1)_{n1}-A^2]$ where n1 is an integer ranging from 1 to 5, $A^1$ and $A^2$ are independently selected from the group consisting of:
  1. a substituted or unsubstituted $C_5$-$C_{18}$ monocyclic or polycyclic aliphatic group,
  2. a substituted or unsubstituted $C_6$-$C_{18}$ mononuclear or polynuclear aromatic group, and $B^1$ is a divalent linking group selected from the group consisting of:
  1. a single bond,
  2. a substituted or unsubstituted $C_1$-$C_{20}$ linear, branched, monocyclic or polycyclic alkylene group,
  3. a substituted or unsubstituted $C_2$ alkenylene group,
  4. a substituted or unsubstituted $C_2$ alkynylene group,
  5. a substituted or unsubstituted $C_6$-$C_{18}$ mononuclear or polynuclear aromatic group,
  6. an oxygen atom,
  7. a sulfur atom,
  8. a —(C=O)— group,
  9. a —[S(=O)$_2$]— group,
  10. a —(S=O)— group,
  11. a —[C(=O)O]— group,
  12. a —[C(=O)NH]— group, and
  13. a —[O(C($R^{51}$)$_2$C($R^{52}$)$_2$O)$_{n2}$]— group, where n2 is an integer ranging from 1 to 6 and $R^{51}$ and $R^{52}$ are independently a hydrogen atom or a substituted or unsubstituted $C_1$-$C_6$ linear or branched alkyl group (e.g., a partially or fully halogen substituted $C_1$-$C_6$ alkyl group), and Y is a tetravalent organic group selected from the group of consisting of $Y^1$ and $Y^2$ where $Y^1$ is one or more of the structures $Y^{1a}$-$Y^{1d}$, where $R^{22}$ to $R^{30}$ are independently H or a substituted or unsubstituted $C_1$-$C_{10}$ linear or branched alkyl group (e.g., a partially or fully halogen substituted $C_1$-$C_{10}$ alkyl group):

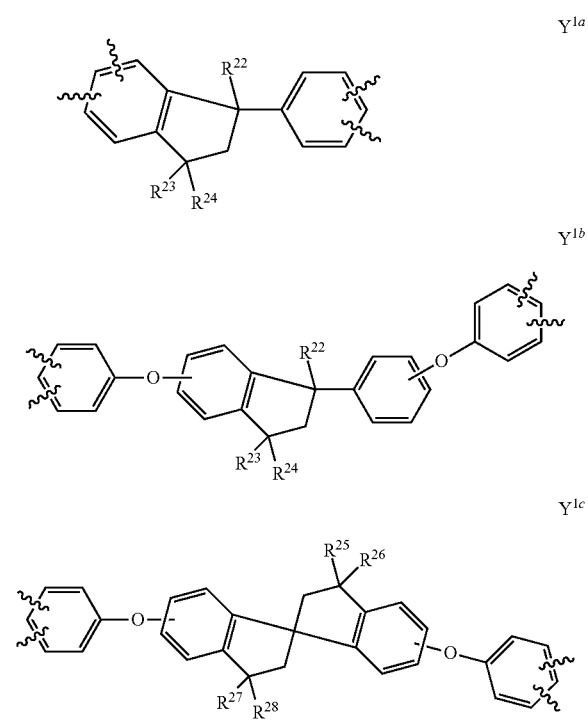

-continued

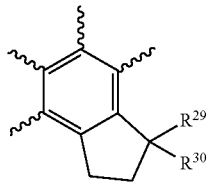
Y$^{1d}$ and Y$^2$ is a tetravalent organic group selected from the group consisting of:
a) a substituted or unsubstituted C$_6$-C$_{18}$ mononuclear or polynuclear aromatic group,
b) a substituted or unsubstituted C$_2$-C$_{18}$ linear, branched, monocyclic or polycyclic alkylene group,
c) a substituted or unsubstituted heterocyclic group,
d) a tetravalent group of Structure V$^a$, V$^b$, V$^c$, V$^d$, V$^e$, V$^f$, V$^g$, V$^h$, V$^i$, or V$^j$, where R$^{31}$ to R$^{41}$ are independently a hydrogen atom or a substituted or unsubstituted C$_1$-C$_{10}$ linear or branched alkyl group (e.g., a partially or fully halogen substituted C$_1$-C$_{10}$ alkyl group) and L$^3$ to L$^6$ are independently selected from the group consisting of an unsubstituted or substituted carbon atom, an oxygen atom, a sulfur atom, a —(C=O)— group, a —[S(=O)$_2$]— group, and a —(S=O)— group:

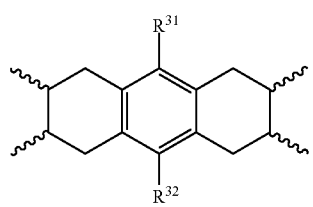
Structure V$^a$

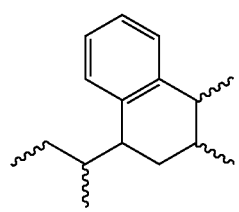
Structure V$^b$

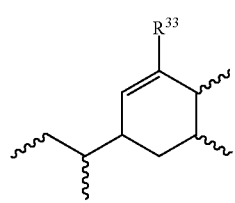
Structure V$^c$

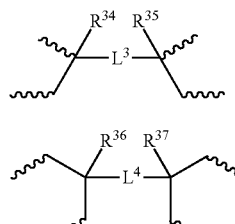
Structure V$^d$

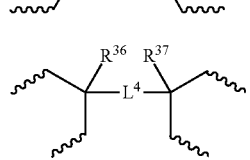
Structure V$^e$

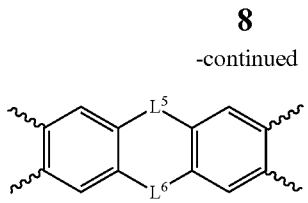
Structure V$^f$

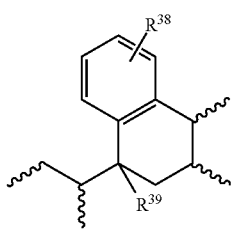
Structure V$^g$

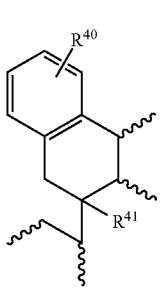
Structure V$^h$

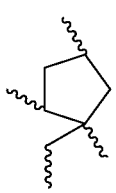
Structure V$^i$

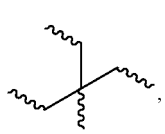
Structure V$^j$ f) a tetravalent group [D$^1$-L$^1$-D$^2$] where D$^1$ and D$^2$ are independently selected from the group consisting of:
1. a substituted or unsubstituted C$_5$-C$_{18}$ monocyclic or polycyclic aliphatic group, and
2. a substituted or unsubstituted C$_6$-C$_{18}$ mononuclear or polynuclear aromatic group, and L$^1$ is a divalent linking group selected from the group consisting of:
1. a single bond,
2. a substituted or unsubstituted C$_1$-C$_{20}$ linear, branched, cyclic or polycyclic alkylene group,
3. a substituted or unsubstituted C$_2$ alkenylene group,
4. a substituted or unsubstituted C$_2$ alkynylene group,
5. a substituted or unsubstituted C$_6$-C$_{18}$ mononuclear or polynuclear aromatic group,
6. an oxygen atom,
7. a sulfur atom,
8. a —(C=O)— group,
9. a —[S(=O)$_2$]— group,
10. a —(S=O)— group,
11. a —[C(=O)O]— group,
12. a —[C(=O)NH]— group, and
13. a —[O(C(R$^{61}$)$_2$C(R$^{62}$)$_2$O)$_{n2}$]— group, where n2 is an integer ranging from 1 to 6 and R$^{61}$ and R$^{62}$ are independently a hydrogen atom or a substituted or unsubstituted $C_1$-$C_6$ linear or branched alkyl group (e.g., a partially or fully halogen substituted $C_1$-$C_6$ alkyl group), in which the mole percent ($X^1+Y^1$) is ≥25% of the total mole percent (X+Y).

In another aspect, the present disclosure features a thermosetting composition that includes a polyimide polymer mentioned herein, at least one multifunctional thiol compound containing at least two thiol groups; at least one solvent; and optionally, at least one non-nucleophilic basic additive.

In some embodiments, the multifunctional thiol compound is of Structure (VI):

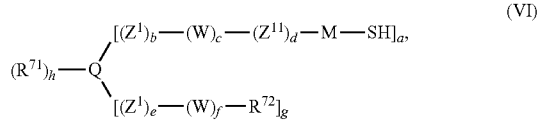

in which a is an integer ranging from 2 to 10; c is an integer ranging from 1 to 10; each of b, d, and e, independently, is an integer ranging from 0 to 1; each of f, g, and h, independently, is an integer ranging from 0 to 10; Q is a multivalent organic nucleus; each of $Z^1$, W, and $Z^{11}$, independently, is a divalent linking group; each of $R^{71}$ and $R^{72}$, independently, is H, a substituted or unsubstituted $C_1$-$C_6$ linear or branched alkyl group, or a substituted or unsubstituted $C_3$-$C_{10}$ cycloaliphatic group; and M is a substituted or unsubstituted $C_1$-$C_6$ linear or branched aliphatic group, a substituted or unsubstituted $C_3$-$C_{10}$ cycloaliphatic group, or a substituted or unsubstituted $C_6$-$C_{18}$ mononuclear or polynuclear aromatic group.

In some embodiments, the composition further includes at least one non-nucleophilic basic additive. For example, the non-nucleophilic basic additive can be a nitrogen-containing compound or a phosphorus-containing compound.

In another aspect, the present disclosure features a thermosetting composition comprising,
  A. at least one polymer of Structure I,
  B. at least one solvent,
  C. optionally a non-nucleophilic basic additive, and
  D. at least one multifunctional thiol of Structure VI described above,
with the proviso that the compounds of Structure VI do not contain an alkoxysilane group.

In another aspect, the present disclosure features a manufacturing process for producing a thermoset coating that includes coating a substrate with a thermosetting composition disclosed herein to form a coated substrate, and baking said coated substrate to cure the thermosetting composition.

In another aspect, the present disclosure features a manufacturing process for producing a thermoset coating, said process comprising
  A. providing a substrate,
  B. coating said substrate with a thermosetting composition of the present disclosure to form a coated substrate, and
  C. baking said coated substrate at a temperature or temperatures for a time sufficient to cure the thermosetting composition.

In some embodiments, coating the substrate includes applying the thermosetting composition on the substrate by ink jet printing, spin coating, spray coating, dip coating, roller coating, or dynamic surface tension coating.

In another aspect, the present disclosure features a device (e.g., a semiconductor device) that includes a coated substrate prepared by the manufacturing process described herein.

DETAILED DESCRIPTION OF THE DISCLOSURE

Definition of Terms

In the context of this disclosure, the term "tetravalent group" used in relation to the polyimide polymer or monomers to synthesize the polymer means that the element contains four bonds (tetravalent) that function as part of the polymer backbone or will become part of an imide group after processing. Other substituents, if allowed, may be present but are not of the type that will be integrated into the backbone or the imide group. The term "divalent group" means that the group is linked to two designated moieties. Any allowed substituents on the divalent group are not of the same type as the designated moieties.

The term "cycloreversion reaction" refers to a reversal reaction of a cycloaddition reaction. An example of a cycloreversion reaction is a retro-Diels-Alder reaction. In some embodiments, the products of a cycloreversion reaction can be formed sequentially or simultaneously.

The terms "one or more" and "at least one" are used interchangeably. The terms "films" and "coatings" are used interchangeably.

The terms "moieties" and "groups" are used interchangeably. Likewise their singulars are used interchangeably.

Detailed Description

The first embodiment of the present disclosure is directed to end-capped polyimide polymers of Structure I.

Structure I

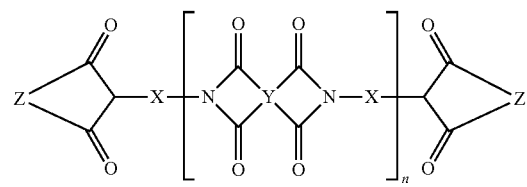

where Z is a divalent organic group capable of undergoing a cycloreversion reaction (e.g., in the solid state at a temperature at most about 250° C.), n is an integer greater than 5, each X, independently, is a divalent organic group selected from one or more of the group of $X^1$ and $X^2$ where $X^1$ is one or more of the structures $X^{1a}$-$X^{1d}$ where $R^{11}$ to $R^{21}$ are independently a substituted or unsubstituted $C_1$-$C_{10}$ linear or branched alkyl group (e.g., a partially or fully halogen substituted $C_1$-$C_{10}$ alkyl group):

$X^{1a}$

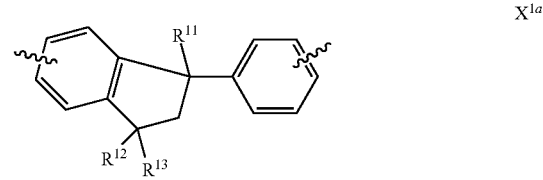

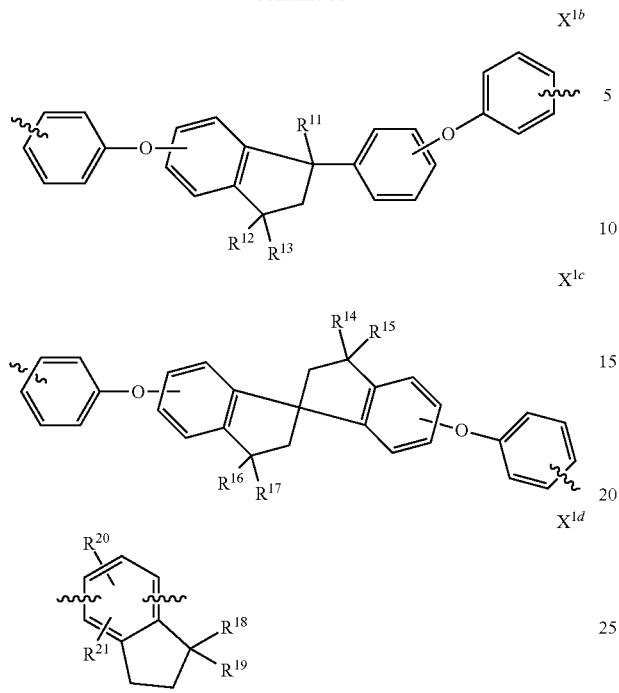

X^{1b}

X^{1c}

X^{1d} and $X^2$ is a divalent organic group selected from the group consisting of:
a) a substituted or unsubstituted $C_6$-$C_{18}$ mononuclear or polynuclear aromatic group,
b) a substituted or unsubstituted $C_1$-$C_{20}$ linear, branched, monocyclic or polycyclic alkylene group,
c) a substituted or unsubstituted heterocyclic group,
d) a linear or branched alkylene group containing one or more oxygen atoms, sulfur atoms, or $NR^{91}$ groups within the chain, in which $R^{91}$ is a $C_1$-$C_3$ alkyl group,
e) a divalent group of Structure IV$^a$, IV$^b$, or IV$^c$,

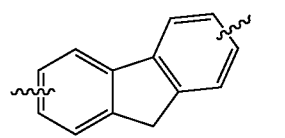

Structure IV$^a$

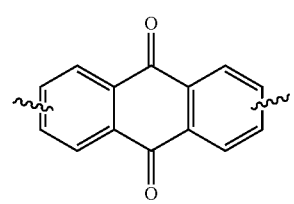

Structure IV$^b$

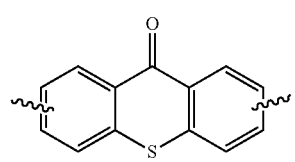

Structure IV$^c$ f) a divalent group $[A^1\text{-}(B^1)_{n1}\text{-}A^2]$ where n1 is an integer ranging from 1 to 5, $A^1$ and $A^2$ are independently selected from the group consisting of:

1. a substituted or unsubstituted $C_5$-$C_{18}$ cyclic or polycyclic aliphatic group, and
2. a substituted or unsubstituted $C_6$-$C_{18}$ mononuclear or polynuclear aromatic group, and $B^1$ is a divalent linking group selected from the group consisting of:
1. a single bond,
2. a substituted or unsubstituted $C_1$-$C_{20}$ linear, branched, monocyclic or polycyclic alkylene group,
3. a substituted or unsubstituted $C_2$ alkenylene group,
4. a substituted or unsubstituted $C_2$ alkynylene group,
5. a substituted or unsubstituted $C_6$-$C_{18}$ mononuclear or polynuclear aromatic group,
6. an oxygen atom,
7. a sulfur atom,
8. a —(C=O)— group,
9. a —[S(=O)$_2$]— group,
10. a —(S=O)— group,
11. a —[C(=O)O]— group,
12. a —[C(=O)NH]— group, and
13. a —[O(C(R$^{51}$)$_2$C(R$^{52}$)$_2$O)$_{n2}$]— group, where n2 ranges from 1 to about 6 and $R^{51}$ and $R^{52}$ are independently a hydrogen atom or a substituted or unsubstituted $C_1$-$C_6$ linear, or branched alkyl group (e.g., a partially or fully halogen substituted $C_1$-$C_6$ alkyl group), and each Y, independently, is a tetravalent organic group selected from the group of consisting of $Y^1$ and $Y^2$ where $Y^1$ is one or more of the structures $Y^{1a}$-$Y^{1d}$, where $R^{22}$ to $R^{30}$ are independently a substituted or unsubstituted $C_1$-$C_{10}$ linear, branched alkyl group (e.g., partially or fully halogen substituted $C_1$-$C_{10}$ alkyl group),

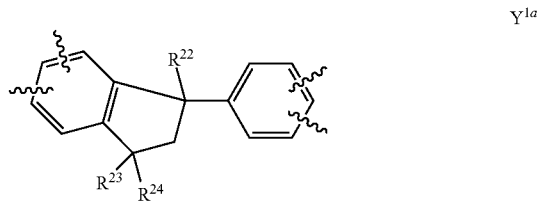

Y$^{1a}$

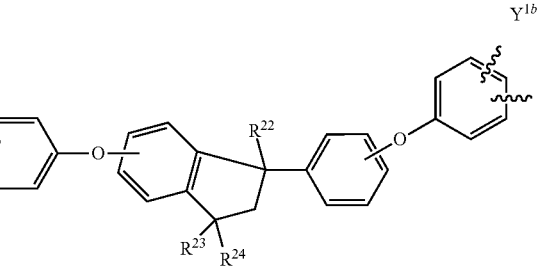

Y$^{1b}$

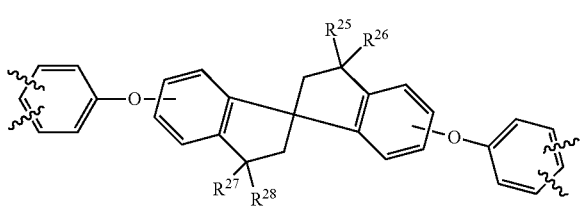

Y$^{1c}$

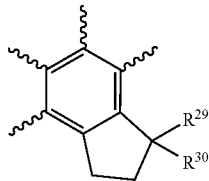
Y$^{1d}$ and Y$^2$ is a tetravalent organic group selected from the group consisting of:
  a) a substituted or unsubstituted C$_6$-C$_{18}$ mononuclear or polynuclear aromatic group,
  b) a substituted or unsubstituted C$_2$-C$_{18}$ linear, branched, monocyclic or polycyclic alkylene group,
  c) a substituted or unsubstituted heterocyclic group,
  d) a tetravalent group of Structure V$^a$, V$^b$, V$^c$, V$^d$, V$^e$, V$^f$, V$^g$, V$^h$, V$^i$, or V$^j$, where R$^{31}$ to R$^{41}$ are independently a hydrogen atom or a substituted or unsubstituted C$_1$-C$_{10}$ linear or branched alkyl group (e.g., a partially or fully halogen substituted C$_1$-C$_{10}$ alkyl group) and L$^3$ to L$^6$ are independently selected from the group consisting of an unsubstituted or substituted carbon atom, an oxygen atom, a sulfur atom, a —(C═O)— group, a —[S(═O)$_2$]— group and a —(S═O)— group:

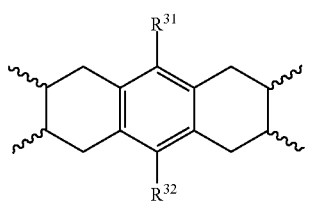
Structure V$^a$

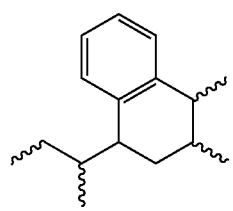
Structure V$^b$

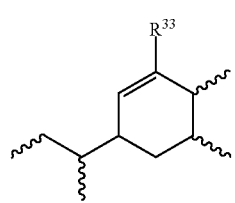
Structure V$^c$

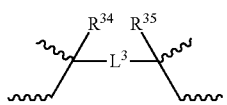
Structure V$^d$

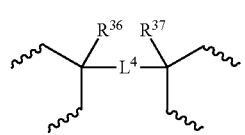
Structure V$^e$

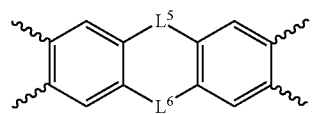
Structure V$^f$

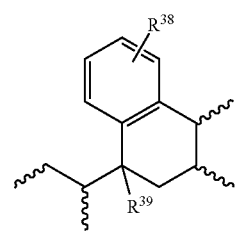
Structure V$^g$

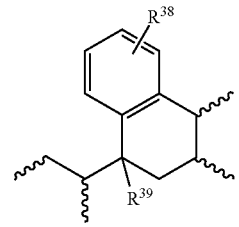
Structure V$^h$

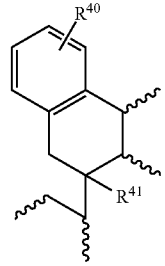
Structure V$^i$

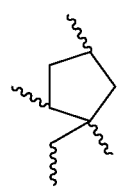
Structure V$^j$

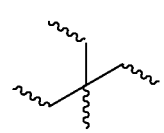

e) a tetravalent group [D$^1$-L$^1$-D$^2$] where, D$^1$ and D$^2$ are independently selected from the group consisting of:
  1. a substituted or unsubstituted C$_5$-C$_{18}$ cyclic or polycyclic aliphatic group, and
  2. a substituted or unsubstituted C$_6$-C$_{18}$ mononuclear or polynuclear aromatic group, and L$^1$ is a divalent linking group selected from the group consisting of:
  1. a single bond,
  2. a substituted or unsubstituted C$_1$-C$_{20}$ linear, branched, cyclic or polycyclic alkylene group,
  3. a substituted or unsubstituted C$_2$ alkenylene group,
  4. a substituted or unsubstituted C$_2$ alkynylene group,
  5. a substituted or unsubstituted C$_6$-C$_{18}$ mononuclear or polynuclear aromatic group,
  6. an oxygen atom,
  7. a sulfur atom,
  8. a —(C═O)— group,
  9. a —[S(═O)$_2$]— group,
  10. a —(S═O)— group,
  11. a —[C(═O)O]— group,
  12. a —[C(═O)NH]— group, and
  13. a —[O(C(R$^{61}$)$_2$C(R$^{62}$)$_2$O)$_{n2}$]— group, where n2 is an integer ranging from 1 to 6 and R$^{61}$ and R$^{62}$ are independently a hydrogen atom or a substituted or unsubstituted C$_1$-C$_6$ linear or branched alkyl group (e.g., a partially or fully halogen substituted C$_1$-C$_6$ alkyl group), in which the mole percent ($X^1+Y^1$) is ≥25% of the total mole percent (X+Y).

In some embodiments, the polymers of Structure I can be prepared by the following three-step process. The first step is polymerization of one or more diamines containing the nucleus X (as defined above) with one or more dianhydrides containing the nucleus Y (as defined above) to produce a polyamic acid (Structure VII). The second step is end-capping of the polyamic acid with a monoanhydride (as defined above) to yield a polyamic acid of Structure VIII containing at least one end-cap group capable of undergoing a cycloreversion reaction (e.g., in the solid state at a temperature at most about 250° C.). The third step is imidization of the end-capped polyamic acid of Structure VIII to yield Structure I. In some embodiments, the polymers of Structure I can be prepared by other suitable processes.

Structure VII

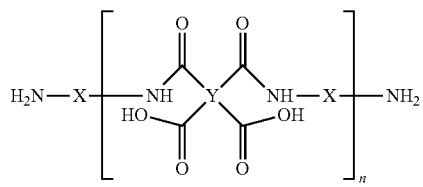

Structure VIII

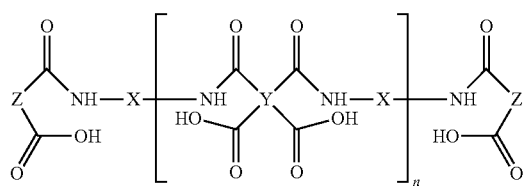

Structure I

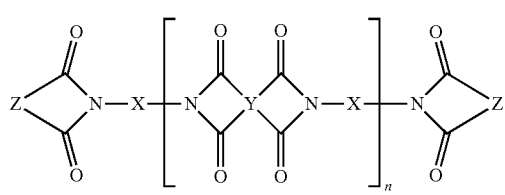

The diamines containing the nucleus X are selected from diamines containing either the nucleus $X^1$ or $X^2$. The nucleus $X^1$ is selected from the group consisting of the structures $X^{1a}$-$X^{1d}$ containing indane structures.

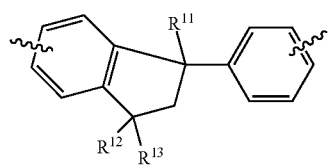

$X^{1a}$

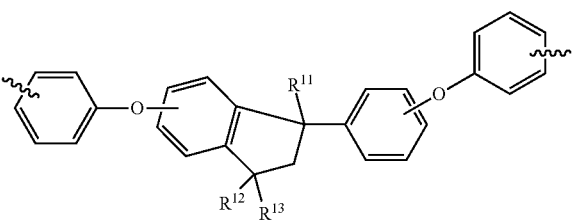

$X^{1b}$

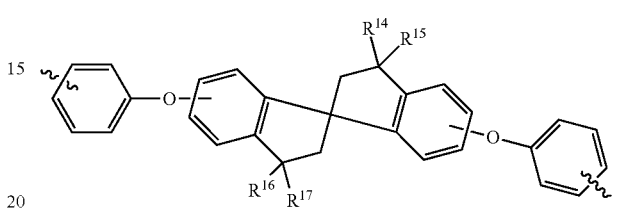

$X^{1c}$

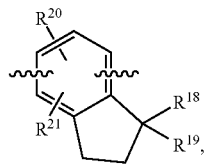

$X^{1d}$ in which $R^{11}$-$R^{21}$ are defined above.

$X^{1a}$, an indane moiety with a phenyl group, can consist of any combination of isomeric or substituted isomeric radicals of the formula $X^{1a}$. Examples of diamines containing Structure $X^{1a}$ include, but are not necessarily limited to, 5-amino-6-methyl-1-(3'-amino-4'-methylphenyl)-1,3,3-trimethylindan, 4-amino-6-methyl-1-(3'-amino-4'-methylphenyl)-1,3,3-trimethylindan, and 5-amino-(1'-amino-2',4'-dimethylphenyl)-1,3,3,4,6-pentamethylindan.

$X^{1b}$, an indane moiety with phenyl ether groups, can likewise consist of any combination of isomeric or substituted isomeric radicals of the formula $X^{1b}$. Examples of diamines containing $X^{1b}$ include, but are not necessarily limited to, 5-(4-aminophenoxy)-3-[4-(4-aminophenoxy)phenyl]-1,1,3-trimethylindan and 5-(3-aminophenoxy)-3-[4-(3-aminophenoxy)phenyl]-1,1,3-trimethylindan.

$X^{1c}$, containing two indane moieties in a spiro relationship and ether groups, can consist of any combination of isomeric or substituted isomeric radicals of the formula $X^{1c}$. Examples of diamines containing $X^1$ include, but are not necessarily limited to, 6,6'-bis(4-aminophenoxy)-3,3,3',3'-tetramethyl-1,1'-spirobiindan and 6,6'-bis(3-aminophenoxy)-3,3,3',3'-tetramethyl-1,1'-spirobiindan.

$X^{1d}$, an indane moiety, can likewise consist of any combination of isomeric or substituted isomeric radicals of the formula $X^{1d}$. Examples of diamines containing $X^{1d}$ include, but are not necessarily limited to, 5,7-diamino-1,1-dimethylindan, 4,7-diamino-1,1-dimethylindan, 5,7-diamino-1,1,4-trimethylindan, 5,7-diamino-1,1,6-trimethylindan, and 5,7-diamino-1,1-dimethyl-4-ethylindan.

Examples of preferred diamines containing one of $X^{1a}$-$X^{1d}$ are 5-amino-6-methyl-1-(3'-amino-4'-methylphenyl)-1,3,3-trimethylindan, 4-amino-6-methyl-1-(3'-amino-4'-methylphenyl)-1,3,3-trimethylindan, 5-amino-(1'-amino-2',4'-dimethylphenyl)-1,3,3,4,6-pentamethylindan, 5-(4-aminophenoxy)-3-[4-(4-aminophenoxy)phenyl]-1,1,3-trimethylindan, and 5-(3-aminophenoxy)-3-[4-(3-aminophenoxy)phenyl]-1,1,3-trimethylindan.

In some embodiments, the diamines having the nucleus $X^2$ have the generic Structure III.

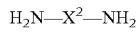

Structure III

The nucleus $X^2$ is a divalent organic group selected from the group consisting of:
  a) a substituted or unsubstituted $C_6$-$C_{18}$ mononuclear or polynuclear aromatic group,
  b) a substituted or unsubstituted $C_1$-$C_{20}$ linear, branched, cyclic or polycyclic alkylene group,
  c) a substituted or unsubstituted heterocyclic group,
  d) a linear or branched alkylene group containing one or more oxygen atoms, sulfur atoms, or $NR^{91}$ groups within the chain, in which $R^{91}$ is a $C_1$-$C_3$ alkyl group,
  e) a divalent group of Structure IV$^a$, IV$^b$, or IV$^c$,

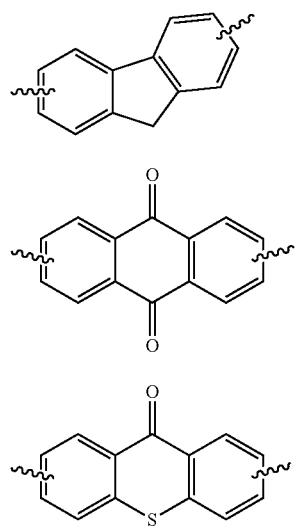

Structure IV$^a$

Structure IV$^b$

Structure IV$^c$ f) a divalent group $[A^1$-$(B^1)_{n1}$-$A^2]$ where n1 is an integer ranging from 1 to 5, $A^1$ and $A^2$ are independently selected from the group consisting of:
    1. a substituted or unsubstituted $C_6$-$C_{18}$ monocyclic or polycyclic alkylene, and
    2. a substituted or unsubstituted $C_6$-$C_{18}$ mononuclear or polynuclear aromatic group, and $B^1$ is a divalent linking group selected from the group consisting of:
    1. a single bond,
    2. a substituted or unsubstituted $C_1$-$C_{20}$ linear, branched, monocyclic or polycyclic alkylene group,
    3. a substituted or unsubstituted $C_2$ alkenylene group,
    4. a substituted or unsubstituted $C_2$ alkynylene group,
    5. a substituted or unsubstituted $C_6$-$C_{18}$ mononuclear or polynuclear aromatic group,
    6. an oxygen atom,
    7. a sulfur atom,
    8. a —(C=O)— group,
    9. a —[S(=O)$_2$]— group,
    10. a —(S=O)— group,
    11. a —[C(=O)O]— group,
    12. a —[C(=O)NH]— group, and
    13. a —[O(C(R$^{51}$)$_2$C(R$^{52}$)$_2$O)$_{n2}$]— group, where n2 ranges from 1 to 6 and R$^{51}$ and R$^{52}$ are independently a hydrogen atom or a substituted or unsubstituted $C_1$-$C_6$ linear, or branched alkyl group (e.g., a partially or fully halogen substituted $C_1$-$C_6$ alkyl group).

Examples of divalent organic functional groups $B^1$ include, but are not limited to, those shown below:

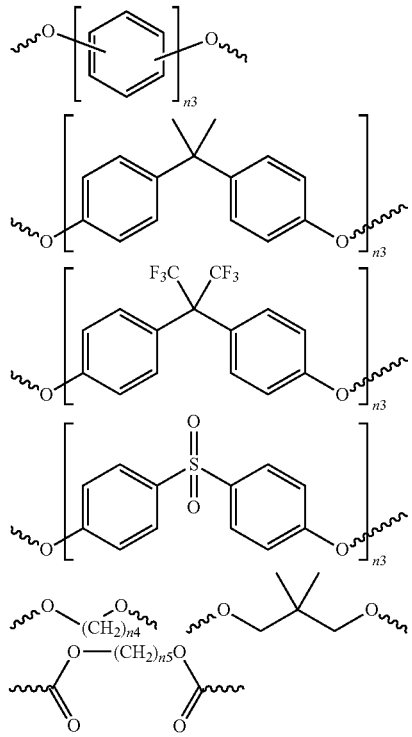

in which each of n3, n4 and n5, independently, is an integer ranging from 1 to 6.

Suitable examples of linear or branched alkylene groups containing one or more oxygen atoms, sulfur atoms, or $NR^{91}$ groups within the chain include, but are not limited to,

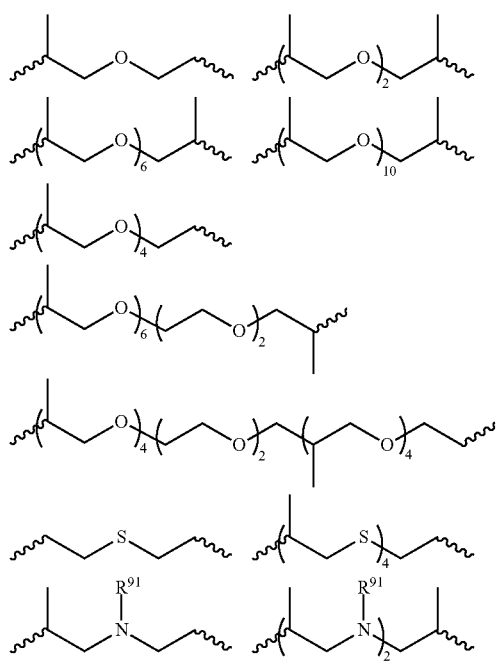

in which $R^{91}$ is a $C_1$-$C_3$ alkyl group (i.e., methyl, ethyl, propyl, or isopropyl).

Suitable examples of $X^2$ include, but are not limited to, the following fragments:

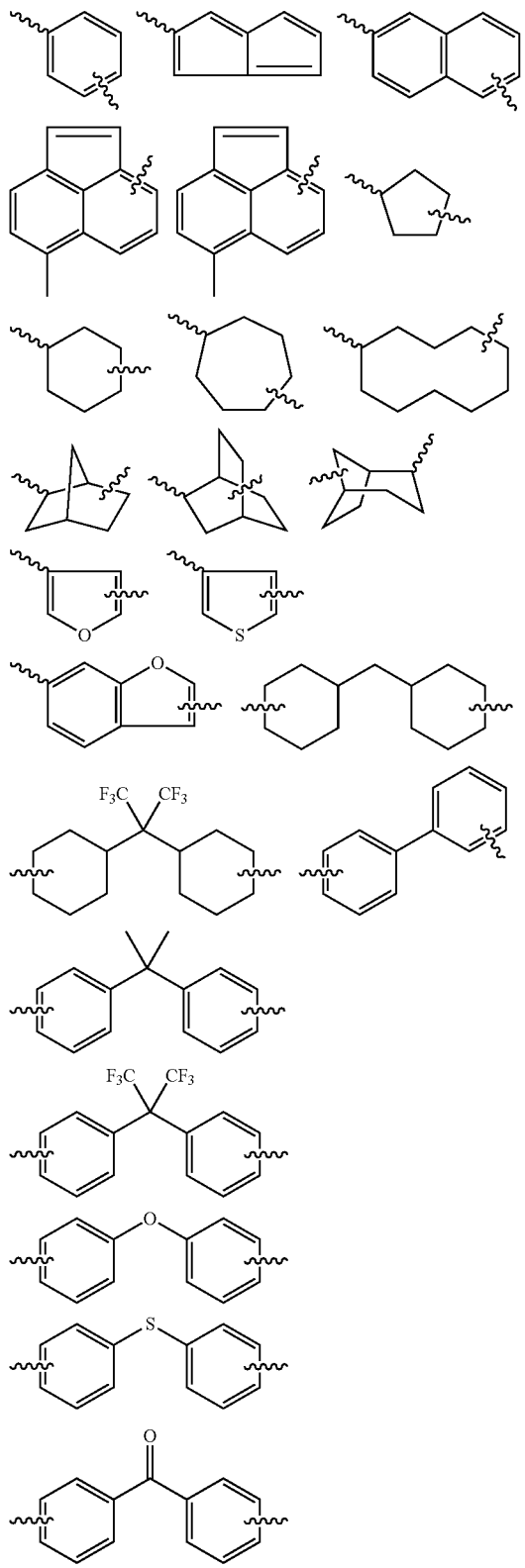

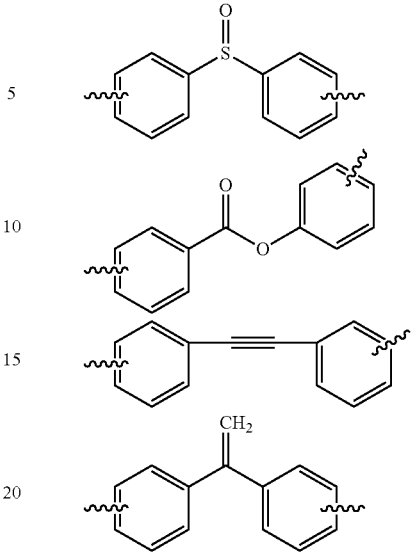

Examples of suitable diamines having the $X^2$ nucleus include, but are not limited to, p-phenylenediamine, m-phenylenediamine, o-phenylenediamine, 1,3-diamino-4,6-diisopropylbenzene, 2,4-diamino-1,3,5-trimethylbenzene, 3-methyl-1,2-benzene-diamine, 2,3,5,6-tetramethyl-1,4-benzenediamine, m-xylenediamine, p-xylenediamine, 1,5-diaminonaphthalene, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,2-diaminocyclohexane, 1,4-diaminocyclohexane, 1,3-cyclohexanebis (methylamine), 5-amino-1,3,3-trimethyl cyclohexanemethanamine, 2,5-diaminobenzotrifluoride, 3,5-diaminobenzotrifluoride, 1,3-diamino-2,4,5,6-tetrafluorobenzene, 4,4'-oxydianiline, 3,4'-oxydianiline, 3,3'-oxydianiline, 3,3'-diaminodiphenylsulfone, 4,4'-diaminodiphenyl sulfones, 4,4'-isopropylidenedianiline, 4,4'-diaminodiphenylmethane, 2,2-bis(4-aminophenyl)propane, 4,4' diaminodiphenyl propane, 4,4'-diaminodiphenyl sulfide, 4,4'-diaminodiphenylsulfone, 4-aminophenyl-3-aminobenzoate, 2,2'-dimethyl-4,4'-diaminobiphenyl, 3,3'-dimethyl-4,4'-diaminobiphenyl, 2,2'-bis (trifluoromethyl) benzidine, 3,3'-bis (trifluoromethyl) benzidine, 2,2-bis [4-(4-aminophenoxy phenyl)] hexafluoropropane, 2,2-bis (3-amino-4-methylphenyl)-hexafluoropropane, 2,2-bis(3-aminophenyl)-1,1, 1,3,3,3-hexafluoropropane, 1,3-bis-(4-aminophenoxy) benzene, 1,3-bis-(3-aminophenoxy)benzene, 1,4-bis-(4-aminophenoxy)benzene, 1,4-bis-(3-aminophenoxy) benzene, 1-(4-aminophenoxy)-3-(3-aminophenoxy) benzene, 2,2'-bis-(4-phenoxyaniline)isopropylidene, N,N-bis(4-aminophenyl)aniline, bis(p-beta-amino-t-butylphenyl) ether, p-bis-2-(2-methyl-4-aminopentyl)benzene, p-bis(1,1-dimethyl-5-aminopentyl)benzene, 3,3'-dimethyl-4,4'-diaminobiphenyl, 3,3'-dimethoxybenzidine, 4,4'-diaminobenzophenone, 3'-dichlorobenzidine, 2,2-bis [4-(4-aminophenoxy)phenyl] propane, 4,4'-[1,3-phenylenebis(1-Methyl-ethylidene)] bisaniline, 4,4'-[1,4-phenylenebis(1-methyl-ethylidene)]bisaniline, 2,2-bis [4-(4-aminophenoxy) phenyl] sulfone, 2,2-bis [4-(3-aminophenoxy) benzene], 1,4-bis (4-aminophenoxy) benzene, 1,3-bis (4-aminophenoxy) benzene, and 1,3'-bis (3-aminophenoxy) benzene, 2,6-diamino-9H-thioxanthen-9-one, 2,6-diaminoanthracene-9,10-dione, and 9H-fluorene-2,6-diamine.

Examples of preferred diamines having the $X^2$ nucleus include, but are not limited to, m-phenylenediamine, 1,3-diamino-4,6-diisopropylbenzene, 2,4-diamino-1,3,5-trimethylbenzene, m-xylenediamine, 1,5-diaminonaphthalene, 2,5-diaminobenzotrifluoride, 3,5-diaminobenzotrifluoride, 4,4'-oxydianiline, 4,4'-diaminodiphenyl sulfones, 2,2-bis(4-aminophenyl)propane, 4-aminophenyl-3-aminobenzoate, 2,2-bis [4-(4-aminophenoxy phenyl)] hexafluoropropane, 2,2-bis (3-amino-4-methylphenyl)-hexafluoropropane, 2,2-bis(3-aminophenyl)-1,1,1,3,3,3-hexafluoropropane, 1,3-bis-(4-aminophenoxy)benzene, 1,3-bis-(3-aminophenoxy)benzene, 1-(4-aminophenoxy)-3-(3-aminophenoxy)benzene, 2,2'-bis-(4-phenoxyaniline)isopropylidene, 3,3'-dimethyl-4,4'-diaminobiphenyl, 3,3'-dimethoxybenzidine, 4,4'-diaminobenzophenone, 2,2-bis [4-(4-aminophenoxy)phenyl] propane, 4,4'-[1,3-phenylenebis(1-Methyl-ethylidene)] bisaniline, 4,4'-[1,4-phenylenebis(1-methyl-ethylidene)] bisaniline, 2,2-bis [4-(4-aminophenoxy) phenyl] sulfone, 2,2-bis [4-(3-aminophenoxy) benzene], 1,3'-bis (3-aminophenoxy) benzene, 2,6-diamino-9H-thioxanthen-9-one, 2,6-diaminoanthracene-9,10-dione, and 9H-fluorene-2,6-diamine.

The dianhydrides containing the nucleus Y are selected from dianhydrides containing either the nucleus $Y^1$ or $Y^2$. The nucleus $Y^1$ is selected from the group consisting of the structures $Y^{1a}$-$Y^{1d}$ (which contains indane structures) where $R^{22}$ to $R^{30}$ are independently H or a substituted or unsubstituted $C_1$-$C_{10}$ linear, branched alkyl group (e.g., a partially or fully halogen substituted $C_1$-$C_{10}$ alkyl group).

$Y^{1a}$, an indane moiety, can consist of any combination of isomeric or substituted isomeric radicals of the formula $Y^{1a}$. Examples of dianhydrides containing $Y^{1a}$ include, but are not limited to, 1-(3',4'-dicarboxyphenyl)-1,3,3-trimethylindan-5,6-dicarboxylic acid dianhydride, 1-(3',4'-dicarboxyphenyl)-1,3,3-trimethylindan-6,7-dicarboxylic acid dianhydride, 1-(3',4'-dicarboxyphenyl)-3-methylindan-5,6-dicarboxylic acid dianhydride, and 1-(3',4'-dicarboxyphenyl)-3-methylindan-6,7-dicarboxylic acid anhydride.

$Y^{1b}$, having an indane ether moiety, can likewise consist of any combination of isomeric or substituted isomeric radicals of the formula $Y^{1b}$. Examples of dianhydrides containing $Y^{1b}$ include, but are not limited to, 5-[4-(1',2'-dicarboxyphenoxy)]-3-[4-(1',2'-dicarboxyphenoxy)phenyl]-1,1,3-trimethylindan dianhydride, 5-[4-(2',3'-dicarboxyphenoxy)]-3-[4-(2',3'-dicarboxyphenoxy)phenyl]-1,1,3-trimethylindan dianhydride and 6-[4-(1',2'-dicarboxyphenoxy)]-3-[4-(1',2'-dicarboxyphenoxy)phenyl]-1,1,3-trimethylindan dianhydride.

$Y^{1c}$, having a spirobindane moiety, can likewise consist of any combination of isomeric or substituted isomeric radicals of the formula $Y^{1c}$. Examples of dianhydrides containing $Y^{1c}$ include, but are not limited to, 6,6'-bis(3,4-carboxyphenoxy)-3,3,3',3'-tetramethyl-1,1'-spirobiindan tetracarboxylic acid dianhydride, 5,5'-bis(3,4-carboxyphenoxy)-3,3,3',3'-tetramethyl-1,1'-spirobiindan tetracarboxylic acid dianhydride and 5-(3,4-carboxyphenoxy)-6-(3',4'-carboxyphenoxy)'-3,3,3',3'-tetramethyl-1,1'-spirobiindan tetracarboxylic acid dianhydride.

$Y^{1d}$, an indane moiety, can likewise consist of any combination of isomeric or substituted isomeric radicals of the formula $Y^{1d}$. Examples of dianhydrides containing $Y^{1d}$ include, but are not limited to, 1,2,3,4-(6,6-dimethylindan) tetracarboxylic acid dianhydride and 1,2,3,4-(7,7-dimethylindan)tetracarboxylic acid dianhydride.

Examples of preferred dianhydrides containing $Y^1$ include, but are not limited to, 1-(3',4'-dicarboxyphenyl)-1,3,3-trimethylindan-5,6-dicarboxylic acid dianhydride, 1-(3',4'-dicarboxyphenyl)-1,3,3-trimethylindan-6,7-dicarboxylic acid dianhydride, 1-(3',4'-dicarboxyphenyl)-3-methylindan-5,6-dicarboxylic acid dianhydride and 1-(3',4'-dicarboxyphenyl)-3-methylindan-6,7-dicarboxylic acid anhydride.

In some embodiments, dianhydrides containing the nucleus $Y^2$ have the generic structure VI

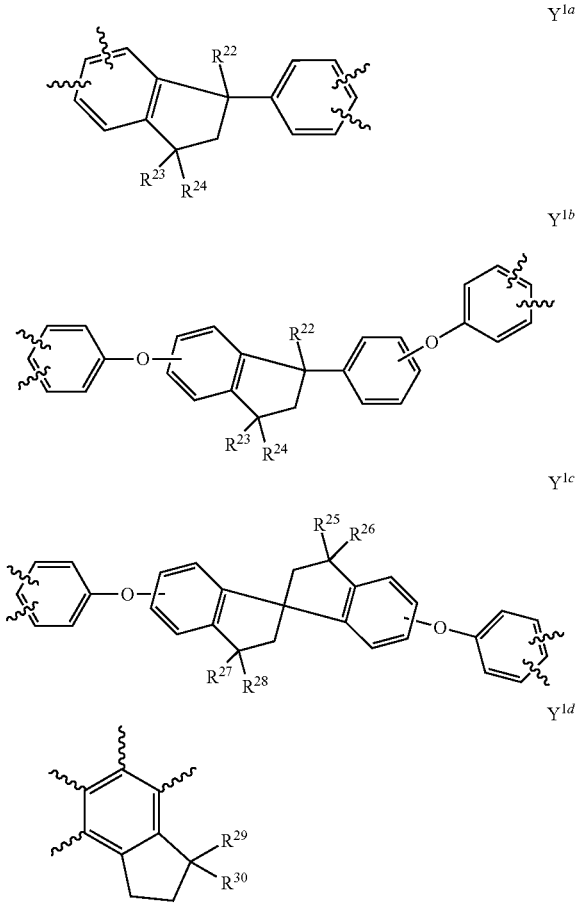

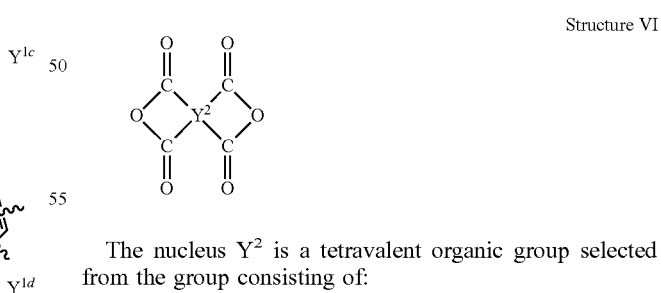

Structure VI

The nucleus $Y^2$ is a tetravalent organic group selected from the group consisting of:
a) a substituted or unsubstituted $C_6$-$C_{18}$ mononuclear or polynuclear aromatic group,
b) a substituted or unsubstituted $C_2$-$C_{18}$ linear, branched, cyclic or fused polycyclic alkylene group,
c) a substituted or unsubstituted heterocyclic group,
d) a tetravalent group of Structure $V^a$, $V^b$, $V^c$, $V^d$, $V^e$, $V^f$, $V^g$, $V^h$, $V^i$, or $V^j$, where $R^{31}$ to $R^{41}$ are independently a hydrogen atom or a substituted or unsubstituted $C_1$-$C_{10}$ linear or branched alkyl group (e.g., a partially or fully halogen substituted $C_1$-$C_{10}$ alkyl group) and $L^3$ to $L^6$ are independently selected from the group consisting of an unsubstituted or substituted carbon atom, an oxygen atom, a sulfur atom, a —(C=O)— group, a —[S(=O)$_2$]— group and a —(S=O)— group, Structure V$^a$
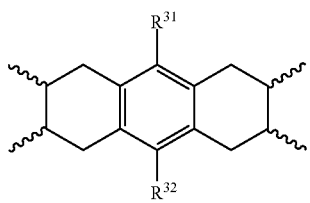

Structure V$^b$
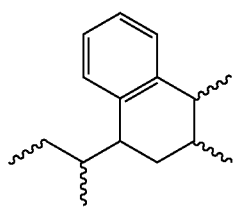

Structure V$^c$
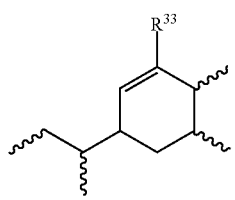

Structure V$^d$
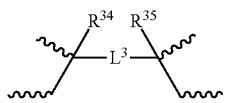

Structure V$^e$
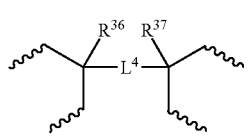

Structure V$^f$
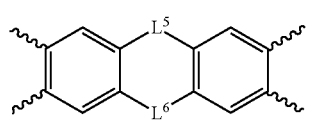

Structure V$^g$
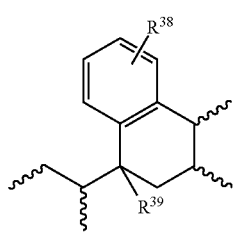

Structure V$^h$
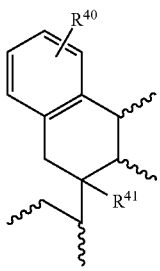

Structure V$^i$
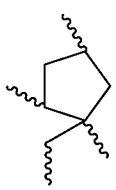

Structure V$^j$
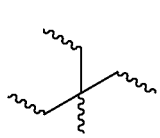

e) a tetravalent group [$D^1$-$L^1$-$D^2$] where, $D^1$ and $D^2$ are independently selected from the group consisting of:
  1. a substituted or unsubstituted $C_5$-$C_{18}$ monocyclic or polycyclic aliphatic group, and
  2. a substituted or unsubstituted $C_6$-$C_{18}$ mononuclear or polynuclear aromatic group, and $L^1$ is a divalent linking group selected from the group consisting of:
  1. a single bond,
  2. a substituted or unsubstituted $C_1$-$C_{20}$ linear, branched, monocyclic or polycyclic alkylene group,
  3. a substituted or unsubstituted $C_2$ alkenylene group,
  4. a substituted or unsubstituted $C_2$ alkynylene group,
  5. a substituted or unsubstituted $C_6$-$C_{18}$ mononuclear or polynuclear aromatic group,
  6. an oxygen atom,
  7. a sulfur atom,
  8. a —(C=O)— group,
  9. a —[S(=O)$_2$]— group,
  10. a —(S=O)— group,
  11. a —[C(=O)O]— group,
  12. a —[C(=O)NH]— group, and
  13. a —[O(C(R$^{61}$)$_2$C(R$^{62}$)$_2$O)$_{n2}$]— group, where n2 ranges from 1 to about 6 and $R^{61}$ and $R^{62}$ are independently a hydrogen atom or a substituted or unsubstituted $C_1$-$C_6$ linear, or branched alkyl group (e.g., a partially or fully halogen substituted $C_1$-$C_6$ alkyl group).

Examples of divalent linking groups $L^1$ include, but are not limited to, those shown below:

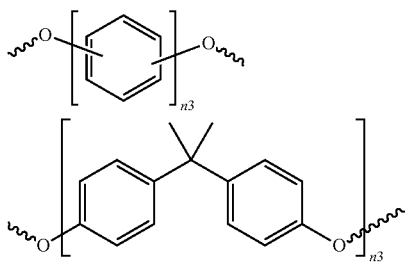

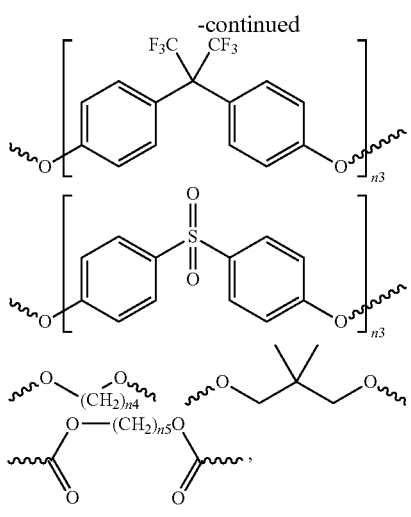
in which n3, n4 and n5 are defined above.
Suitable examples of $Y^2$ include, but are not limited to, the following fragments:
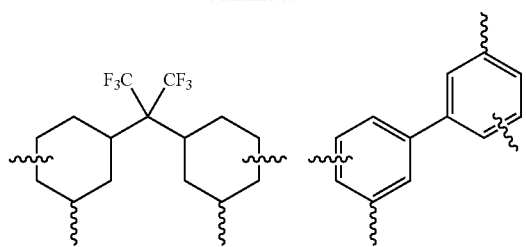
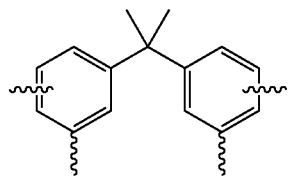
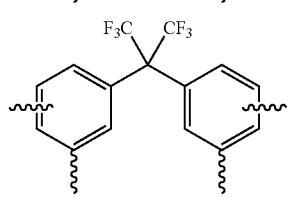
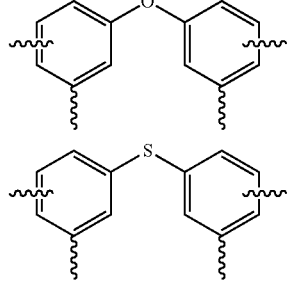
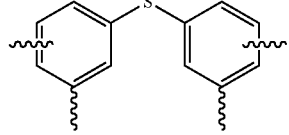
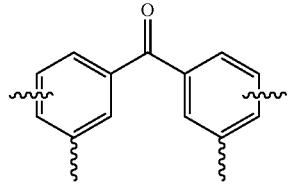
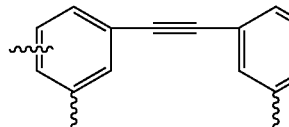
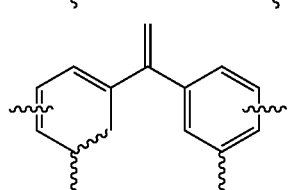
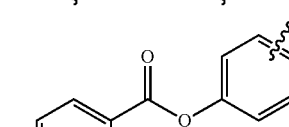
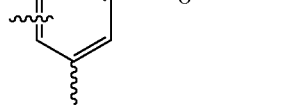

-continued

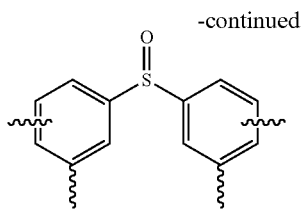

Examples of suitable dianhydride monomers having the Y² nucleus include, but are not limited to, pyromellitic dianhydride, benzene-1,2,3,4-tetracarboxylic dianhydride, 2,3,5,6-naphthalenetetracarboxylic acid dianhydride, 2,3,6,7-naphthalenetetracarboxylic acid dianhydride, 1,4,5,8-naphthalenetetracarboxylic acid dianhydride, 2,6-dichloronaphthalene-1,4,5,8-tetracarboxylic dianhydride, 2,7-dichloronaphthalene-1,4,5,8-tetracarboxylic dianhydride, 2,3,6,7-tetrachloronaphthalene-1,4,5,8-tetracarboxylic dianhydride, phenanthrene-8,9,10-tetracarboxylic dianhydride, 3,4,9,10-perylenetetracarboxylic acid dianhydride, pyrazine-2,3,5,6-tetracarboxylic dianhydride, thiophene-2,3,4,5-tetracarboxylic dianhydride, 2,3,5,6-pyridinetetracarboxylic acid dianhydride, butane-1,2,3,4-tetracarboxylic acid dianhydride, 1,2,3,4-cyclopentanetetracarboxylic acid dianhydride, cyclobutane-1,2,3,4-tetracarboxylic acid dianhydride, cyclopentane-1,2,3,4-tetracarboxylic acid dianhydride, cyclohexane-1,2,4,5-tetracarboxylic acid dianhydride, norbornane-2,3,5,6-tetracarboxylic acid dianhydride, bicyclo[2.2.2]oct-7-ene-3,4,8,9-tetracarboxylic acid dianhydride, tetracyclo[4.4.1.0$^{2,5}$.0$^{7,10}$]undecane-1,2,3,4-tetracarboxylic acid dianhydride, 3,3',4,4'-benzophenone tetracarboxylic dianhydride, 2,2',3,3'-benzophenone tetracarboxylic dianhydride, 2,3,3',4'-benzophenone tetracarboxylic dianhydride, 3,3',4,4'-diphenylsulfone tetracarboxylic dianhydride, 2,2',3,3'-diphenylsulfone tetracarboxylic dianhydride, 2,3,3',4'-diphenylsulfone tetracarboxylic dianhydride, 3,3',4,4'-diphenyl ether tetracarboxylic dianhydride, 2,2',3,3'-diphenyl ether tetracarboxylic dianhydride, 2,3,3',4'-diphenyl ether tetracarboxylic dianhydride, 2,2-[bis(3, 4-dicarboxyphenyl)] hexafluoropropane dianhydride, ethyleneglycol bis(anhydrotrimellitate), and 5-(2,5-dioxotetrahydro)-3-methyl-3-cyclohexene-1,2-dicarboxylic anhydride.

Examples of preferred dianhydride monomers having the Y² nucleus include, but are not limited to, pyrazine-2,3,5,6-tetracarboxylic dianhydride, thiophene-2,3,4,5-tetracarboxylic dianhydride, 2,3,5,6-pyridinetetracarboxylic acid dianhydride, norbornane-2,3,5,6-tetracarboxylic acid dianhydride, bicyclo[2.2.2]oct-7-ene-3,4,8,9-tetracarboxylic acid dianhydride, tetracyclo[4.4.1.0$^{2,5}$.0$^{7,10}$]undecane-1,2,3,4-tetracarboxylic acid dianhydride, 3,3',4,4'-benzophenone tetracarboxylic dianhydride, 3,3',4,4'-diphenylsulfone tetracarboxylic dianhydride, 3,3',4,4'-diphenyl ether tetracarboxylic dianhydride, 2,3,3',4'-diphenyl ether tetracarboxylic dianhydride, 2,2-[bis(3,4-dicarboxyphenyl)] hexafluoropropane dianhydride, ethyleneglycol bis(anhydrotrimellitate), and 5-(2,5-dioxotetrahydro)-3-methyl-3-cyclohexene-1,2-dicarboxylic anhydride.

In some embodiments, a polymer of Structure I can be a polymer containing predominantly one repeating unit (e.g., containing a moiety formed by the condensation reaction between a diamine and a dianhydride). In such embodiments, a polymer of Structure I can be prepared by using one diamine containing the nucleus X as defined above (e.g., X¹ or X²) with one dianhydride containing the nucleus Y as defined above (e.g., Y¹ or Y²) as starting materials, in which at least one of the diamine and dianhydride includes an indane-containing moiety, followed by end-capping with a monoanhydride as defined above and imidization. Exemplary monomer combinations that can make polymers of Structure I containing predominantly one repeating unit are shown in Table A below.

In some embodiments, a polymer of Structure I can be a polymer containing predominantly two or more different repeating units (e.g., each containing a moiety formed by the condensation reaction between a diamine and a dianhydride). In some embodiments, a polymer of Structure I can be prepared by using two or more diamines containing the nucleus X as defined above (e.g., X¹ or X²) with one dianhydride containing the nucleus Y as defined above (e.g., Y¹ or Y²) as starting materials, in which at least one of the diamines and dianhydride includes an indane-containing moiety, followed by end-capping with a monoanhydride as defined above and imidization. In some embodiments, a polymer of Structure I can be prepared by using one diamine containing the nucleus X as defined above (e.g., X¹ or X²) with two or more dianhydrides containing the nucleus Y as defined above (e.g., Y¹ or Y²) as starting materials, in which at least one of the diamine and dianhydrides includes an indane-containing moiety, followed by end-capping with a monoanhydride as defined above and imidization. In some embodiments, a polymer of Structure I can be prepared by using two or more diamines containing the nucleus X as defined above (e.g., X¹ or X²) with two or more dianhydrides containing the nucleus Y as defined above (e.g., Y¹ or Y²) as starting materials, in which at least one of the diamines and dianhydrides includes an indane-containing moiety, followed by end-capping with a monoanhydride as defined above and imidization. Exemplary monomer combinations that can make polymers of Structure I containing predominantly two or more different repeating units are shown in Table A below.

Diamine monomers with the substructure X¹ can be prepared by synthetic methods detailed in, e.g., U.S. Pat. Nos. 3,856,752, 3,983,092, JP61-254543 and U.S. Pat. No. 4,734,482, or through other common organic synthetic methods known to one skilled in the art. Dianhydride monomers with the substructure Y¹ can be prepared by synthetic methods detailed in, e.g., U.S. Pat. Nos. 3,856,752 and 5,047,487, or through other common organic synthetic methods known to one skilled in the art. Numerous diamine monomers with the substructure X² and dianhydride monomers with the substructure Y² are commercially available from a variety of sources including Chriskev Company (Lenexa, Kans., USA) or alternatively may be prepared through common organic synthetic methods known to one skilled in the art.

The polyamic acid of Structure VII may be synthesized by numerous synthetic procedures variations of those procedures known to those skilled in the art. In general, the synthetic procedure brings one or more diamines in contact with one or more dianhydrides in the presence of a solvent suitable to dissolve the monomers, and, preferably, the resultant polyamic acid.

Structure VII

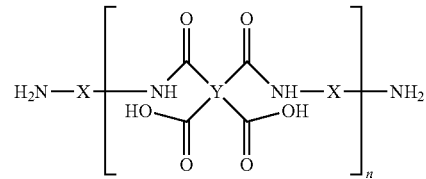

In some embodiments, to prepare a polyamic acid, the diamine component and dianhydride component are charged into a reaction vessel by a method of charging both the components at the same time or a method of gradually charging one of the components in the form of solid or solution into a solution of the other component (complete dissolution of all materials might not occur). The method of charging both the components at the same time is advantageous in view of the productivity because the time required for charging is shortened. The molar ratio of diamine component(s) to dianhydride component(s) is preferably from between 1.01 to 1.40. More preferably, a molar ratio of diamine to dianhydride of about 1.05 to 1.33 is employed. Generally, the reaction is carried out at about 15° C. to about 80° C. for about 1 to about 48 hours. Note that when the molar ratio of diamine component(s) to dianhydride component(s) is greater than 1.00, the resulting species is an amino-terminated polyamic acid, which can be further reacted with an end-capping monomer (e.g., a monoanhydride containing a group capable of undergoing a cycloreversion reaction) to form an end-capped polymer.

Suitable polymerization solvents useful in the present invention include, but are not limited to, N-methyl-2-pyrrolidone, N,N-dimethylformamide, dimethylsulfoxide, gamma-butyrolactone, N,N-dimethylacetamide, tetramethylene sulfone, p-chlorophenol, m-cresol, diethyleneglycol methyl ether, methyl-3-methoxyproprionate, ethyl-3-ethoxypropionate, cyclohexanone, propylene glycol monomethyl ether acetate, and 2-chloro-4-hydroxytoluene. These solvents may be used singly or in combination of two or more. Of these solvents, preferred are N-methyl-2-pyrrolidone, gamma-butyrolactone and N,N-dimethylacetamide, with N-methyl-2-pyrrolidone being more preferred. In some embodiments, a poor solvent for the polyimide may be used in combination with these solvents in such an amount to not allow the polyamic acid to precipitate. Examples of such a poor solvent include hexane, heptane, benzene, toluene, xylene, chlorobenzene and o-dichlorobenzene. The amount of the poor solvent to be used is preferably 50 percent by weight or less (inclusive of zero) based on the total amount of the solvents. The polyamic acid thus produced may be isolated by precipitation into a non-solvent or a poor solvent and collected by filtration.

The second step of the synthetic process towards the polymer of Structure I mentioned above is to end-cap the polyamic acid of Structure VII synthesized in the first step. In some embodiments, the second step can be carried out by reacting an amino-terminated polyamic acid of Structure VII with a monoanhydride of Structure IX to yield an end-capped polyamic acid of Structure VIII. In some embodiments, the end-capped polyamic acid thus formed can be used for further reaction without isolation.

In some embodiments, the monoanhydride suitable for preparing the polyamic acid of Structure VIII contains a "masked" maleic anhydride group, which after conversion of the anhydride group to an imide group, becomes a "masked" maleimide group. This imide group in the polymer of Structure I is able to undergo a cycloreversion reaction (e.g., a retro-Diels-Alder reaction) to unmask the maleimide group. A polyimide polymer containing maleimide groups as end-cap groups can react with a cross-linking agent (e.g., a compound containing at least two thiol groups) to form a cross-linked polyimide.

Examples of monoanhydrides that can undergo a cycloreversion reaction include, but are not limited to, compounds described by Structure IX.

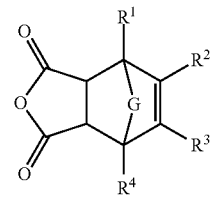

Structure IX where G is —O—, —(NR$^{100}$)—, —[C(R$^{101}$)=C(R$^{102}$)]—, or —[C=C(R$^{103}$)$_2$]—, in which each of R$^{100}$, R$^{101}$, R$^{102}$, and R$^{103}$ independently, is H, a substituted or unsubstituted C$_1$-C$_{12}$ linear, branched, monocyclic or polycyclic alkyl group, or a substituted or unsubstituted phenyl group, and each of R$^1$, R$^2$, R$^3$ and R$^4$, independently, is H, a substituted or unsubstituted C$_1$-C$_{12}$ linear, branched, monocyclic or polycyclic alkyl group, a substituted or unsubstituted phenyl group, OR$^{104}$, CH$_2$OR$^{105}$, CH$_2$OC(=O)R$^{106}$, CH$_2$C(=O)OR$^{107}$, CH$_2$NHR$^{108}$, CH$_2$NHC(=O)R$^{109}$, CH$_2$C(=O)N(R$^{110}$)$_2$, C(=O)OR$^{111}$, in which each of R$^{104}$, R$^{105}$, R$^{106}$, R$^{107}$, R$^{108}$, R$^{109}$, R$^{110}$ and R$^{111}$, independently, is H or a substituted or unsubstituted C$_1$-C$_6$ linear, branched, or monocyclic alkyl group.

Examples of anhydrides of Structure IX include, but are not limited to, Structures IX$^a$, IX$^b$, IX$^c$, or IX$^d$:

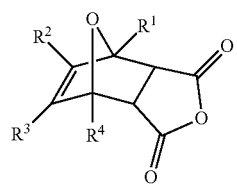

IX$^a$

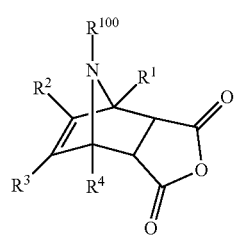

IX$^b$

Structure VIII

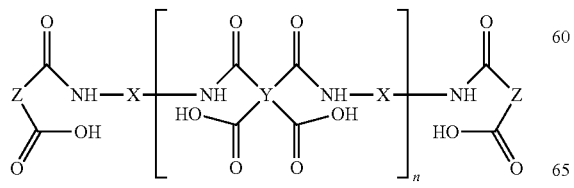

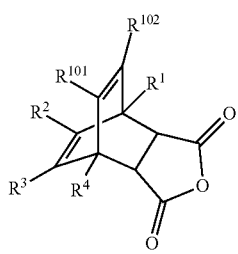

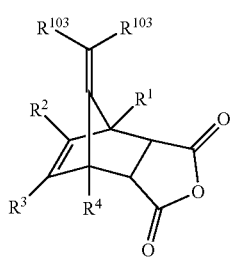

in which R¹-R⁴ and R¹⁰⁰-R¹⁰³ are defined above.

Examples of specific suitable monoanhydrides of Structure IX include, but are not limited to the following compounds.

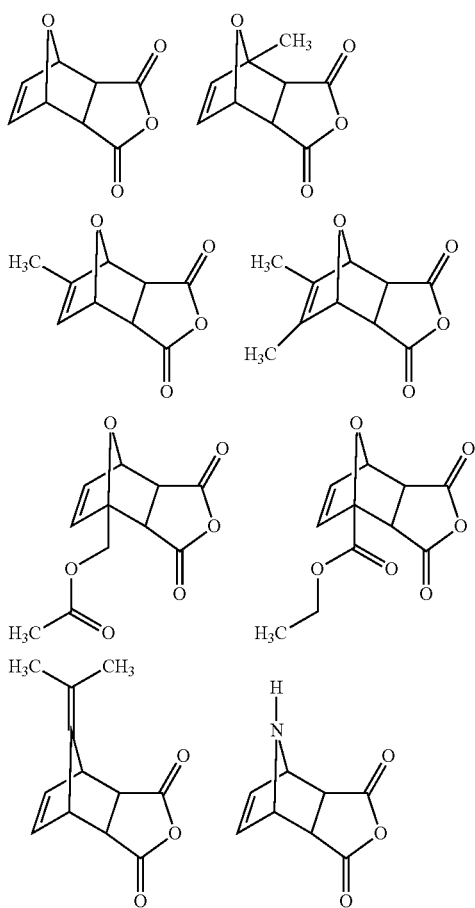

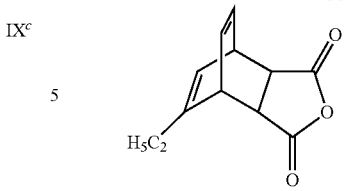

Generally, the reaction of a polyamic acid of Structure VII with a monoanhydride of Structure IX is carried out at about 10° C. to about 70° C. for about 3 to about 48 hours in the presence of a basic catalyst. Examples of suitable basic catalysts include, but are not limited to, pyridine, triethylamine, tripropylamine, tributylamine, dicyclohexylmethylamine, 2-methylpyridine, 2,6-lutidine, 3,5-lutidine, picoline, 4-dimethylaminopyridine (DMAP) and the like. In general, the basic catalyst should not be a compound capable of degrading the polyamic acid backbone. Examples of compounds capable of degrading the polyamic acid backbone include, but are not limited to, primary and secondary amines. The amount of monoanhydride used is about 1.01 to 1.25 molar equivalent of theoretical unreacted amine functionality on the amino-terminated polyamic acid. Preferably, the amount of monoanhydride used is about 1.01 to 1.15 molar equivalent of unreacted amine functionality on the amino-terminated polyamic acid. More preferably, the amount of monoanhydride used is about 1.05 to 1.10 molar equivalent of unreacted amine functionality on the amino-terminated polyamic acid. The monoanhydride is added to the reaction mixture as a solid or solution in a suitable solvent. The preferred solvent is the reaction solvent. The basic catalyst is typically added to the polyamic acid solution after addition of the monoanhydride. Preferably, the basic catalyst can be used in the same molar equivalent as the monoanhydride used for the reaction mixture.

In some embodiments, in the third step of the synthetic process towards Structure I, a chemical imidizing agent (dehydrating agent) is added to the end-capped polyamic acid of Structure VIII, which catalyzes the ring-closing dehydration process of the polyamic acid groups to form imide functionalities on both the backbone and the endcap groups, thereby forming an end-capped polyimide.

Examples of suitable dehydrating agents include, but are not limited to, trifluoromethane sulfonic acid, methanesulfonic acid, p-toluenesulfonic acid, ethanesulfonic acid, butanesulfonic acid, perfluorobutanesulfonic acid, acetic anhydride, propionic anhydride, and butyric anhydride. In addition, this dehydration process can be catalyzed by further addition of a basic catalyst. If used, the basic catalyst employed can be the same as or different from the basic catalyst employed in the end-capping reaction described above.

In some embodiments, the chemical imidization process is carried out with a suitable dehydrating reagent and a basic catalyst at about 60° C. to about 130° C. for about 6 to about 48 hours. The dehydrating agent and basic catalyst are employed typically in equimolar concentrations. About 90 to 200% (molar) dehydrating agent is typically used based on total amic acid present in the polymerizing mixture to complete the cyclization reaction. Preferably, 120 to 160% (molar) dehydrating agent is used to complete the amic acid cyclization process.

Evidence of complete imidization and formation of a polyimide of Structure I may be confirmed by observation of characteristic absorptions in the infrared spectrum from 1770 and 1700 cm$^{-1}$ attributable to the imide ring structure.

In some embodiments, the resulting polyimide of Structure I may be isolated by precipitation into water and/or an organic solvent, recovered by filtration and dried. Alternatively, the polyimide of Structure I may be isolated by the addition of water and a suitable low boiling, water-immiscible solvent. Because of the lower polarity nature of the indane moieties in the polyimide polymer, higher solubility in lower polarity water immiscible solvents allows the polyimide, unlike most polyimides, to be extracted from the higher polarity reaction solvent/water mixture. This extracted polymer solution may be purified by washing with water followed by separation of the water layer, distillation of various volatile compounds, and subsequent extraction into a higher boiling solvent. Preferably the higher boiling solvent is also the precipitating solvent for the composition of the present disclosure.

It should be noted that molecular weight and inherent viscosity of the polymers and therefore, X and Y at a constant stoichiometry, can have a wide range depending on the reaction conditions chosen and considerations (such as the purity of the solvent, the humidity, presence or absence of a blanket of nitrogen or argon gas, reaction temperature, reaction time, and other variables). However, these factors should be controlled in order to achieve polymers with the desired amounts of the indane structure and molecular weights.

In general, the molar amount of indane structures in the polymer of Structure I ($X^1+Y^1$) should range from 25 molar % to about 100 molar % of the molar amount of (X+Y). In some embodiments, the molar amount of ($X^1+Y^1$) ranges from about 25% (e.g., about 35%, about 45%, or about 50%) to about 60% (e.g., about 70%, about 85%, or about 100%). In some embodiments, the molar amount of ($X^1+Y^1$) ranges from about 25% (e.g., about 30%, about 35%, or about 40%) to about 45% (e.g., about 50%, about 55%, or about 60%). In some embodiments, the molar amount of ($X^1+Y^1$) ranges from about 35% (e.g., about 45%, about 55%, or about 65%) to about 70% (e.g., about 85%, about 95%, or about 100%). In some embodiments, the molar amount of ($X^1+Y^1$) ranges from about 50% (e.g., about 55%, about 60%, or about 65%) to about 70% (e.g., about 80%, about 90%, or about 100%).

In some embodiments, $X^1$ ranges from 0% (e.g., about 5%, about 15%, about 20%, or about 30%) to about 58.3% (e.g., about 50.5%, about 45%, about 40%, or about 35%) of the molar amount of (X+Y).

In some embodiments, $Y^1$ ranges from 0% (e.g., about 10%, about 20%, about 30%, or about 35%) to about 49.5% (e.g., about 49%, about 41.7%, about 35%, or about 25%) of the molar amount of (X+Y).

As described previously, the indane structure can be incorporated into the polymer backbone either through the diamine monomer ($X^1$) or the dianhydride monomer ($Y^1$). In some instances, it is preferable that the indane substructure be incorporated exclusively through $X^1$, exclusively through $Y^1$, or through a combination of $X^1$ and $Y^1$. When a combination of $X^1$ and $Y^1$ is employed, suitable ratios of $X^1:Y^1$ range from about 99:1 to about 1:99. Additional suitable ranges are from about 90:10 to about 10:90, from about 80:20 to about 20:80, from about 75:25 to about 25:75, from about 65:35 to about 35:65, from about 60:40 to about 40:60, and about 50:50.

The amount of (X+Y) can be calculated by dividing the numeric average molecular weight (Mn) of a polymer of Structure I by the average molecular weight of the repeat unit. The value of Mn can be determined by such standard methods as membrane osmometry or gel permeation chromatography as described, for example, in Jan Rabek, Experimental Methods in Polymer Chemistry, John Wiley & Sons, New York, 1983.

Suitable weight average molecular weight (Mw) ranges for the polyimide of Structure I range from about 1,000 g/mol to about 50,000 g/mol. Preferred molecular weight ranges may depend on the particular product application, solvent employed, and method of applying to the underlying substrate. For example, suitable weight average molecular weight values for inkjet applications can be at least about 1,000 g/mol (e.g., at least about 9,000 g/mol, at least about 12,000 g/mol, at least about 15,000 g/mol, at least about 20,000 g/mol, at least about 25,000 g/mol, or at least about 35,000 g/mol) and/or can be at most about 50,000 g/mol (e.g., at most about 40,000 g/mol, at most about 35,000 g/mol, at most about 30,000 g/mol, at most about 25,000 g/mol, at most about 20,000 g/mol, at most about 15,000 g/mol, at most about 12,000 g/mol). In some embodiments, n in Structure I is an integer greater than 5 (e.g., from 6 to 50, from 6 to 30, from 10 to 50, or from 10 to 30).

In some embodiments, the polymer of Structure I has the following structure (Structure II).

Structure II

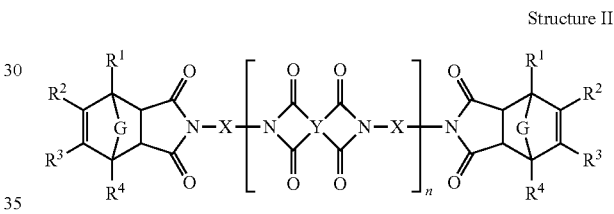

in which n, X, Y, G, and $R^1$-$R^4$ are as defined above. In some embodiments, the polymers of Structure II are synthesized using combinations of one or more $X^1$ containing monomers selected from the group consisting of

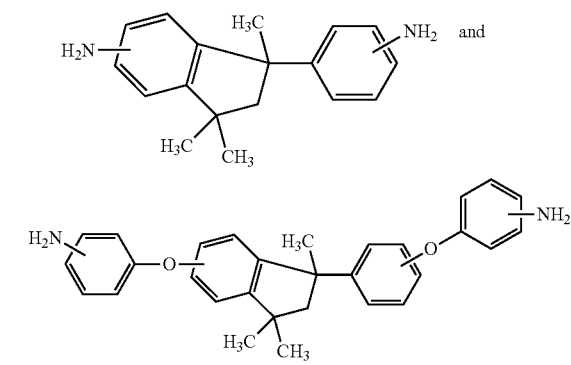

and/or one or more $X^2$ containing monomers selected from the group consisting of

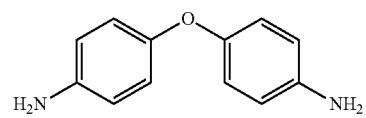

-continued

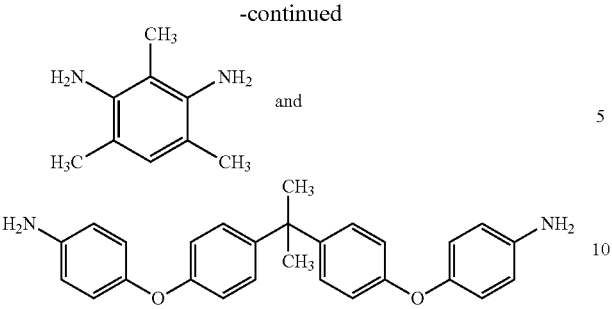

and with a $Y^1$ containing monomer of the following structure

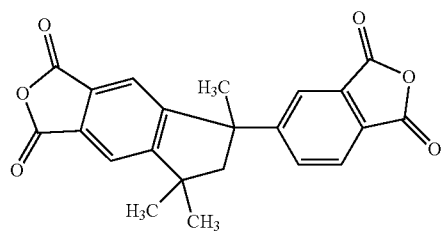 [SMILES: CC1(C)CC(C)(c2ccc3c(c2)C(=O)OC3=O)c2cc3c(cc21)C(=O)OC3=O]

and/or one or more $Y^2$ containing monomers selected from the group consisting of

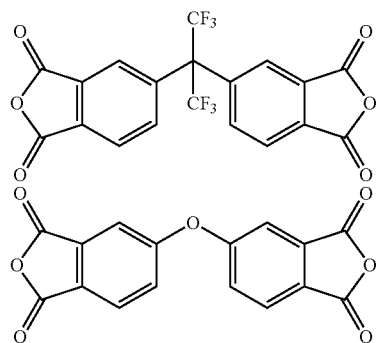

-continued

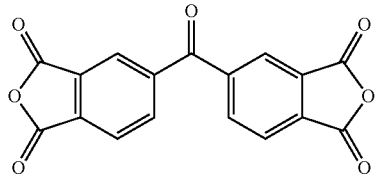

and

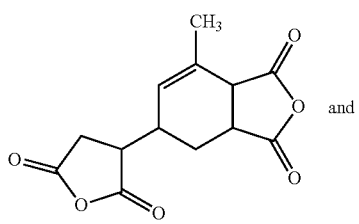

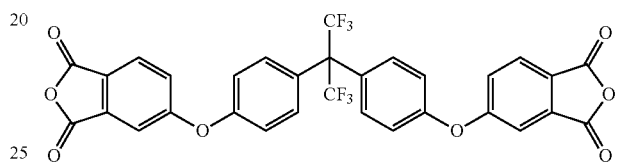

with one or more monoanhydrides selected from the group consisting of

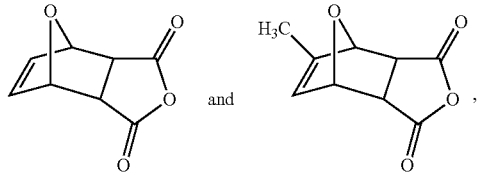

in which the mole percent of $(X^1+Y^1)$ is ≥25% of the total mole percent $(X+Y)$ and the ratio of X:Y is from about 1.01 to about 1.4. Specific illustrations of some of the combinations of these embodiments are shown below in Table A.

TABLE A
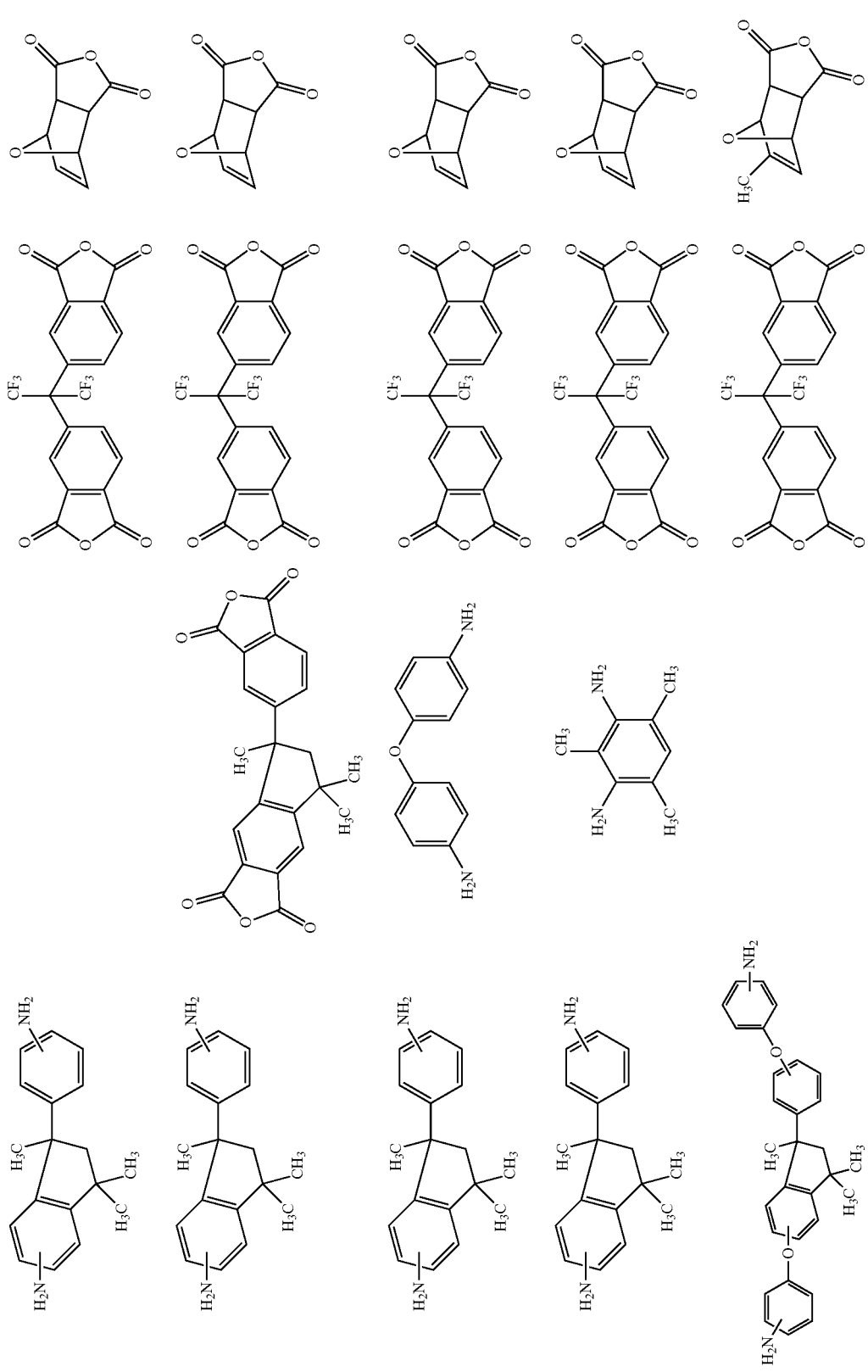

TABLE A-continued
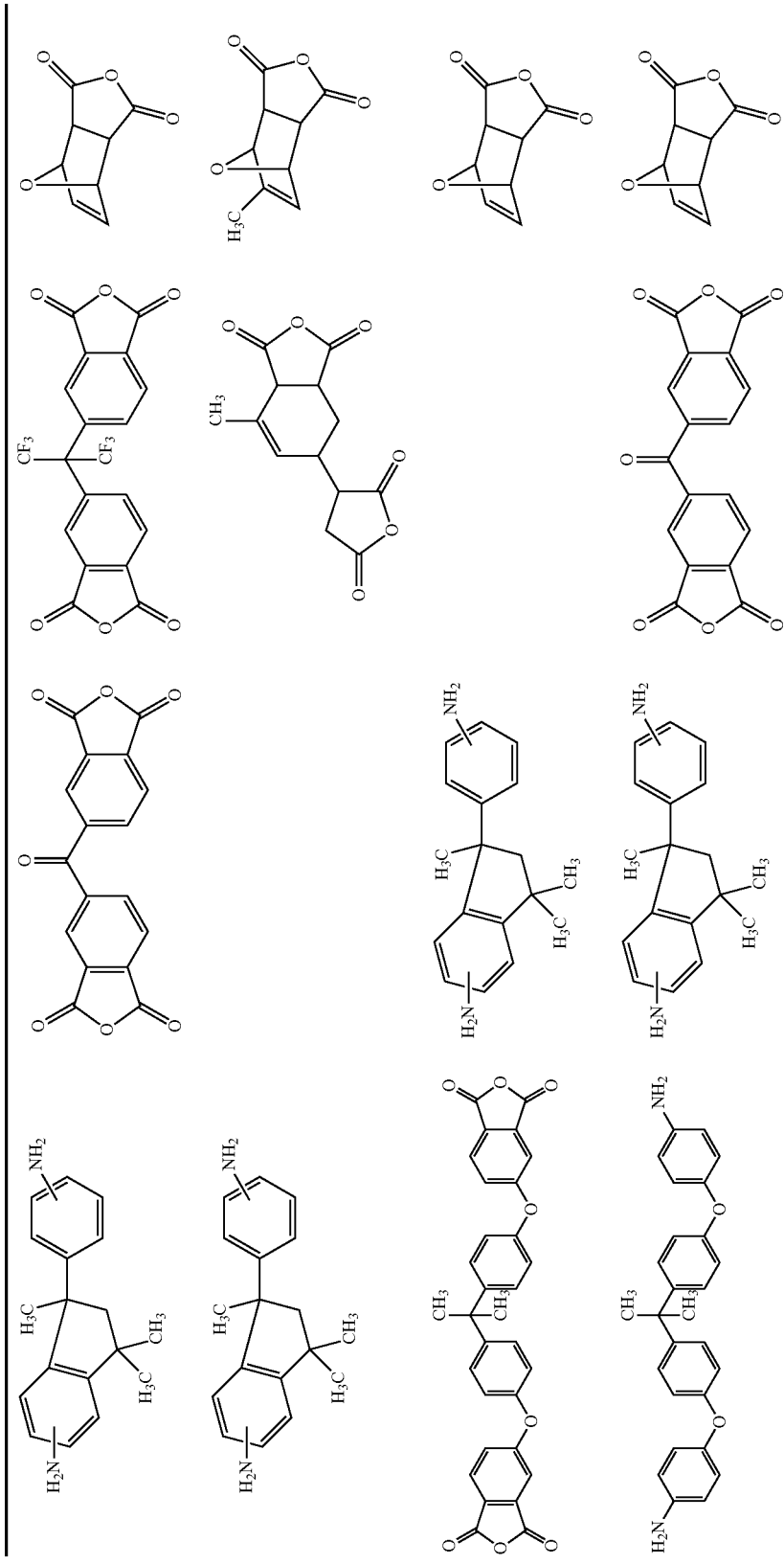

TABLE A-continued
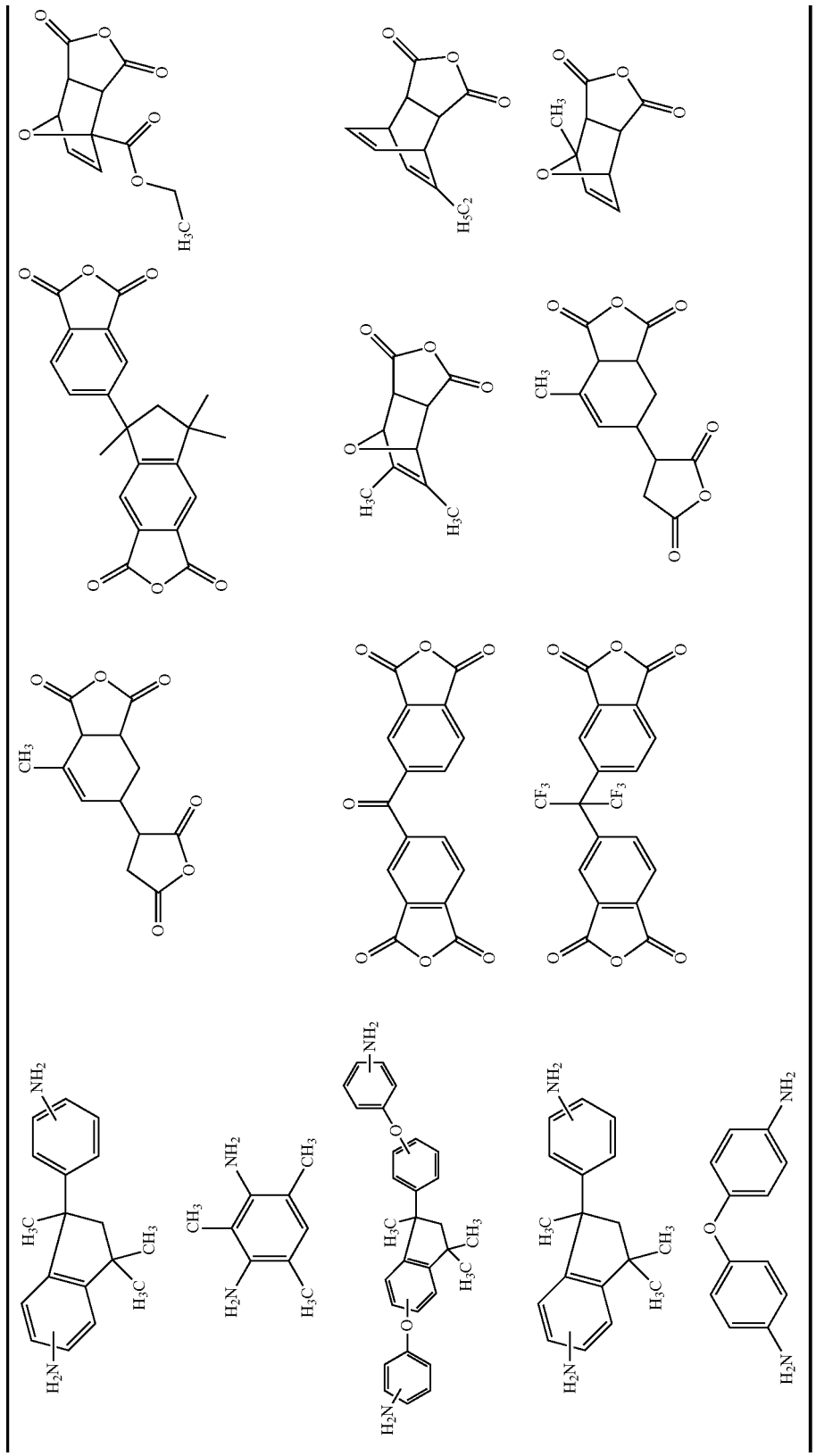

The polyimide polymers described herein generally have excellent solubility in organic solvents, including solvents of lower polarity. In particular, this results in improved performance over prior art polyimide compositions in inkjet applications because the polyimide polymers described herein provide more flexibility in choice of solvents, allow easy adjustment of the viscosity of the thermosetting solution, increase the amount of polymer applied per drop, minimize clogging of ink jet nozzles, and maximize the amount of allowable rest times between periods of application without clogging the ink jet nozzles.

The present disclosure is also directed to a thermosetting composition comprising,
- A. at least one polyimide polymer described herein (e.g., a polymer of Structure I),
- B. at least one solvent,
- C. optionally a non-nucleophilic basic additive, and
- D. at least one multifunctional thiol compound containing at least two thiol groups (which can function as a cross-linker), such as a compound of Structure VI,

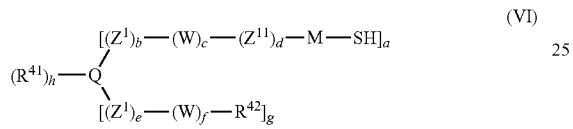

in which a is an integer ranging from 2 to 10; c is an integer ranging from 1 to 10; each of b, d, and e, independently, is an integer ranging from 0 to 1; each of f, g, and h, independently, is an integer ranging from 0 to 10; Q is a multivalent organic nucleus; each of $Z^1$, W, and $Z^{11}$, independently, is a divalent linking group; each of $R^{71}$ and $R^{72}$, independently, is H, a substituted or unsubstituted, linear or branched $C_1$-$C_6$ alkyl group, or a substituted or unsubstituted $C_3$-$C_{10}$ cycloaliphatic group; and M is a substituted or unsubstituted $C_1$-$C_6$ linear or branched aliphatic group, a substituted or unsubstituted $C_3$-$C_{10}$ cycloaliphatic group, or a substituted or unsubstituted $C_6$-$C_{18}$ mononuclear or polynuclear aromatic group. In some embodiments, the compounds of Structure VI do not contain an alkoxysilane group.

In general, a ranges from 2 (e.g., 3, 4, 5, 6) to 10 (e.g., 9, 8, 7, 6), f, g and h independently range from 0 (e.g., 1, 2, 3, 4, 5) to 10 (e.g., 9, 8, 7, 6, 5), and c ranges from 1 (e.g., 2, 3, 4, 5) to 10 (e.g., 9, 8, 7, 6).

Examples of $Z^1$ and $Z^{11}$ include, but are not limited to, —O—, —S—, —O—(C=O)—, —(C=O)—, —(C=O)—O—, —NH—(C=O)—, and —(C=O)—NH—.

The divalent organic bridging group, W, is a bridging group that connects Q to a thiol group or other organic functional group via $Z^1$ and $Z^{11}$. Preferably, W is selected from the group consisting of:
1. a substituted or unsubstituted $C_1$-$C_{12}$ linear, branched, monocyclic, or polycyclic alkylene optionally containing one or more oxygen, sulfur, or nitrogen atoms;
2. a substituted or unsubstituted phenylene;
3. a substituted or unsubstituted $C_3$-$C_6$ mononuclear heteroarylene containing one or more oxygen, sulfur, or nitrogen atoms;
4. a substituted or unsubstituted $C_{10}$-$C_{30}$ polynuclear arylene; and
5. a substituted or unsubstituted $C_7$-$C_{30}$ polynuclear heteroarylene containing one or more oxygen, sulfur, or nitrogen atoms.

Preferably, Q is selected from the group consisting of:
1. an unsubstituted $C_2$-$C_{40}$ linear, branched, monocyclic, or polycyclic aliphatic group optionally containing one or more oxygen, sulfur, or nitrogen atoms; and
2. an unsubstituted $C_2$-$C_{40}$ aliphatic group containing both cyclic and acyclic components and optionally containing one or more oxygen, sulfur, or nitrogen atoms.

Examples of Q include, but are not limited to,

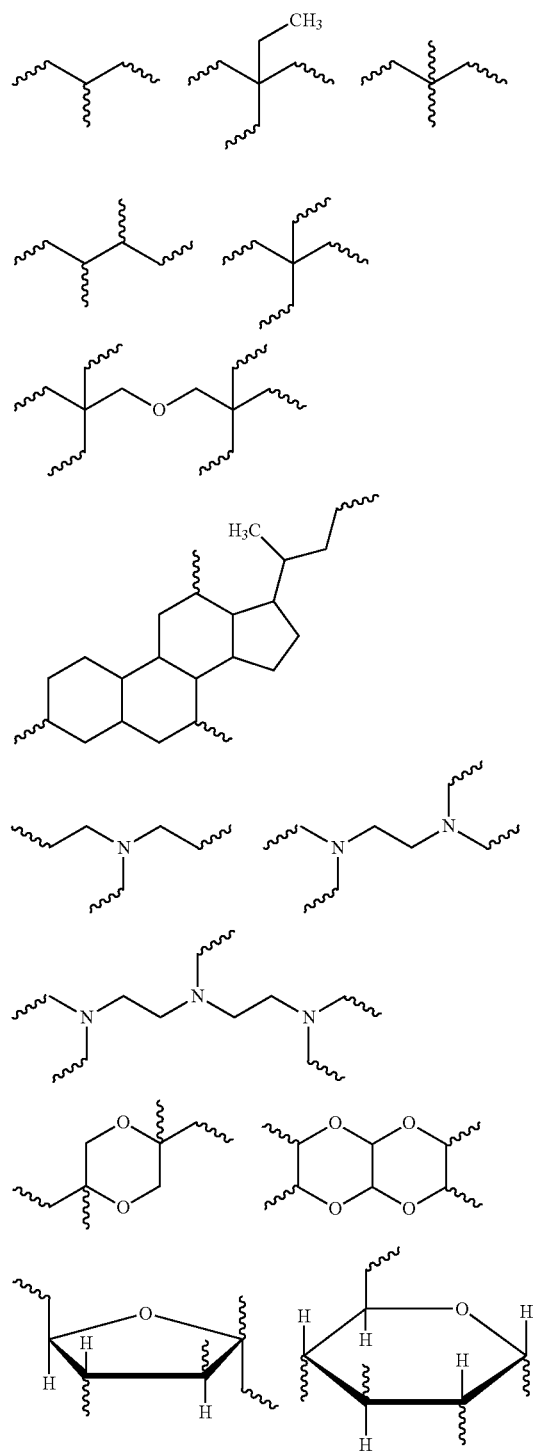

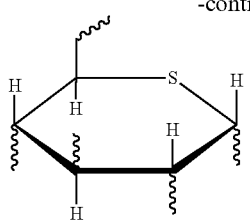

Some examples of specific thiol compounds suitable in thermosetting compositions of the present disclosure include, but are not limited to, trimethylolpropane tris(mercaptoacetate), pentaerythritol tetrakis(mercaptoacetate), trimethylolpropane tris(3-mercaptopropionate), pentaerythritol tetrakis(3-mercaptopropionate), dipentaerythritol hexakis(3-mercaptopropionate), tris[2-(3-mercaptopropionyloxy)ethyl] Isocyanurate, ethoxylated trimethylolpropane tri-3-mercaptopropionate, propylene glycol-3-mercaptopropionate 800, trimethylolpropane tris(4-sulfanylcyclohexanecarboxylate), pentaerythritol tetrakis(4-sulfanylcyclohexanecarboxylate) and the like.

Suitable solvents of this thermosetting composition may include alcohol, ketones, lactones, ethers, amide, imide and esters. The solvent typically should dissolve all components of the thermosetting composition, cast a good film and should not interfere with the crosslinking reaction of the composition. Suitable examples of organic solvents include, but are not limited to, gamma-butyrolactone (GBL), N-methyl-2-pyrrolidone, dimethylimidazolidinone, N-methylcaprolactam, N-methylpropionamide, N,N-dimethylacetamide, dimethyl sulfoxide, N,N-dimethylformamide, N,N-diethylfornamide, diethylacetamide, methyl ethyl ketone, methyl isobutyl ketone, 2-heptanone, cyclopentanone, cyclohexanone, n-butyl acetate, propylene glycol methyl ether acetate (PGMEA), propylene glycol methyl ether (PGME), ethyl lactate, propyl lactate, 3-methyl-3-methoxybutanol, tetralin, isophorone, ethylene glycol monobutyl ether, diethylene glycol monoethyl ether, diethylene glycol monoethyl ether acetate, diethylene glycol dimethyl ether, diethylene glycol methylethyl ether, triethylene glycol monoethyl ether, dipropylene glycol monomethyl ether, methyl 3-methoxypropionate, ethyl 3-ethoxypropionate, diethyl malonate, ethylene glycol 1,4:3,6-dianhydrosorbitol 2,5-dimethyl ether (2,5-dimethylisosorbide), 1,4:3,6-dianhydrosorbitol 2,5-diethyl ether (2,5-diethylisosorbide) and mixtures thereof. More preferred solvents are gamma-butyrolactone, propylene glycol monomethyl ether, 2-heptanone, propylene glycol monomethyl ether acetate, n-butyl acetate, ethyl lactate, and cyclohexanone. These solvent may be used individually or in combination of two or more to improve coating quality of thermosetting composition.

The choice of solvent for the thermosetting composition and the concentration thereof depends principally on the coating method used and the solid used in formulation. The solvent should be inert (e.g., should not undergo any chemical reaction with the components) and should be removable on drying after coating. In the thermosetting composition of the present disclosure, the amount of a solvent or a mixture of solvents as the component in the entire composition can be at least about 40 wt % of the entire mass of the thermosetting composition. For example, the amount of the solvent or mixture of solvents can range from about 40 to about 98 wt % (e.g., from about 85 wt % to about 98 wt %, from about 88 wt % to about 97 wt %, from about 90 wt % to about 95 wt %, from about 50 wt % to about 97 wt %, or from about 60 wt % to about 96 wt %) based on the entire mass of thermosetting composition.

In some embodiments, the amount of polyimide polymer(s) described herein in a single solvent or a mixture of solvents is from about 1 wt % to about 50 wt % (e.g., from about 1 wt % to about 10 wt %, from about 1.5 wt % to about 8 wt %, from about 2 wt % to about 6 wt %, from about 5 wt % to about 50 wt %, from about 10 wt % to about 45 wt %, or from about 20 wt % to about 45 wt %) of the total weight of composition. In general, the weight percentage of a polyimide polymer in a formulation depends on the coating method to be used by the thermosetting composition. Polyimide polymers described herein can be used singly or be combined in any ratio in a thermosetting composition.

In some embodiments, the amount of the multifunctional thiol compound ranges from about 0.2 wt % to about 30 wt % (e.g., from about 0.2 wt % to about 6 wt %, from about 0.5 wt % to about 4 wt %, from about 0.8 wt % to about 3 wt %, from about 1 wt % to about 30 wt %, from about 2 wt % to about 25 wt %, or from about 5 wt % to about 25 wt %) of the total weight of the thermosetting composition.

Thermosetting compositions of the present disclosure may optionally contain at least one non-nucleophilic basic additive. One purpose of the non-nucleophilic basic additive is to act as a catalyst to aid in thermosetting the coating during the final bake step, enabling the curing to be completed at a lower temperature. In generally, the nucleophilicity of the basic additive should be at such a low degree that it will not initiate nucleophilic attack on the imide group of the polyimide. In some embodiments, the total amount of the non-nucleophilic basic additive in the thermosetting composition, when present, is from about 0.002 wt % to about 2 wt % (e.g., from about 0.002 wt % to about 0.4 wt %, from about 0.01 wt % to about 0.2 wt %, from about 0.01 wt % to about 2 wt %, or from about 0.05 wt % to about 1 wt %) of the total composition.

In some embodiments, the non-nucleophilic basic additive is selected from the group consisting of:
a) non-nucleophilic nitrogen-containing basic compounds, and
b) non-nucleophilic phosphorus-containing basic compounds.

In some embodiments, the non-nucleophilic nitrogen-containing basic compound is selected from the group consisting of:
a) non-nucleophilic amines,
b) non-nucleophilic amidines, and
c) non-nucleophilic imines.

In some embodiments, the non-nucleophilic phosphorus-containing basic compound is selected from the group consisting of:
a) non-nucleophilic phosphines,
b) non-nucleophilic phosphites,
c) non-nucleophilic proazaphosphatranes, and
d) non-nucleophilic phosphazenes.

Examples of suitable non-nucleophilic nitrogen-containing basic compounds include, but are not limited to, N,N-dicyclopentylmethylamine, N,N-dicyclopentylethylamine, N,N-dimethylcyclohexylamine, N,N-dicyclohexylmethylamine, N,N-dicyclohexylethylamine, N,N-dicyclohexylbutylamine, N,N-dicyclohexyl-t-butylamine, 1-dimethylaminoadamantane, 1-diethylaminoadamantane, 2-dimethylaminoadamantane, 2-methylimidazole, triethylamine, tripropylamine, tributylamine, triisopropylamine, trihexylamine, trioctylamine, tridodecylamine, 2,4,5-triphenylimidazole, 1,4-diazabicyclo[4.3.0]non-5-ene, 1,5-diazabicyclo[4.3.0]non-5-ene, 1,8-diazabicyclo[5.4.0]undec-7-ene, 1,1,3,3-tetramethylguanidine, pyridine, 2-methylpyridine, 2,6-lutidine, 3,5-lutidine, 1,4-diazabicylco[2.2.2]octane, and picoline. Examples of suitable non-nucleophilic phosphorus-containing basic compounds include, but are not limited to, N'-tert-butyl-N,N,N',N',N'',N''-hexamethylphosphorimidic triamide, 2-tert-butylimino-2-diethylamino-1,3-dimethyl-perhydro-1,3,2-diazaphosphorine, tert-octylimino-tris(dimethylamino)phosphorane, tert-butylimino-tri(pyrrolidino)phosphorane, 2,5,8,9-tetraaza-1-phosphabicyclo[33.3]undecane, 2,8,9-tris(1-methylethyl)], and 2,8,9-triisobutyl-2,5,8,9-tetraaza-1-phosphabicyclo[3.3.3]undecane.

In some embodiments, the non-nucleophilic basic additive may be activated thermally and/or photochemically. Those activated thermally are known as thermal base generators (TBGs) while those activated photochemically are known as photobase generators (PBGs). One skilled in the art would know the appropriate TBG and/or PBG, if any, to employ in compositions of the present disclosure, if desired.

Other additives such as adhesion promoters, surfactants, and plasticizers, but not limited to these, may be added to the thermosetting composition. The amount of additional additives may range from 0% to about 15%.

Suitable adhesion promoters are described in "Silane Coupling Agent" Edwin P. Plueddemann, 1982 Plenum Press, New York. Classes of adhesion promoters include, but are not limited to, vinylalkoxysilanes, methacryloxyalkoxyysilanes (e.g. 3-methacryl-oxypropyldimethoxy-methylsilane, and 3-methacryloxypropyltrimethoxysilane), mercaptoalkoxysilanes, aminoalkoxysilanes, epoxyalkoxysilanes and glycidyloxyalkoxysilanes.

Examples of suitable adhesion promoters which may be employed in the thermosetting composition may be described by Structure XIV.

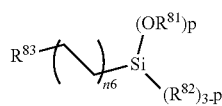

Structure XIV in which each $R^{81}$ and $R^{82}$ are independently a substituted or unsubstituted $C_1$-$C_{10}$ linear or branched alkyl group or a $C_3$-$C_{10}$ cycloalkyl group, p is an integer from 1 to 3 and n6 is an integer from 1 to 6, $R^{83}$ is one of the following moieties:

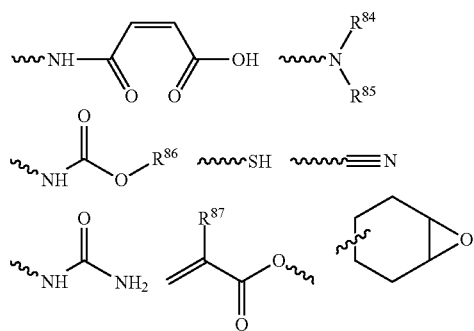

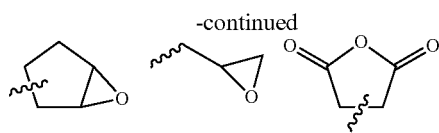

in which each $R^{84}$, $R^{85}$, $R^{86}$ and $R^{87}$ are independently a $C_1$-$C_4$ alkyl group or a $C_5$-$C_7$ cycloalkyl group.

Preferred adhesion promoters are those in which $R^{83}$ is selected from:

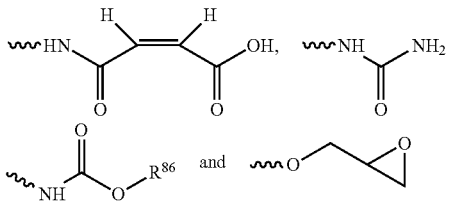

Examples of suitable adhesion promoters having Structure XIV include, but are not limited to, gamma-aminopropyltrimethoxysilane, gamma-glycidyloxypropylmethyldimethoxysilane, gamma-glycidyloxypropylmethyldiethoxysilane, glycidyloxypropyltrimethoxysilane, and gamma-mercaptopropyl-methyldimethoxysilane.

In some embodiments, the adhesion promoter contains a silicon compound without a thiol group. In some embodiments, the adhesion promoter contains a silicon compound without an acrylic moiety. In some embodiments, the adhesion promoter contains a silicon compound without an epoxy group.

in some embodiments, the concentration of the optional adhesion promoter, if employed, ranges from about 0.02 wt % to about 5 wt % (e.g., from about 0.02 wt % to about 1 wt %, from about 0.04 wt % to about 0.5 wt %, from about 0.06 wt % to about 0.4 wt %, from about 0.1 wt % to about 5 wt %, from about 0.2 wt % to about 1.5 wt %, or from about 0.3 wt % to about 1 wt %) of total weight of the thermosetting composition.

The thermosetting compositions of this disclosure may also optionally contain at least one surfactant. If a surfactant is employed, it can be added from about 0.001 to about 2 wt % and preferably from about 0.01 to about 1 wt % based on total weight of the thermosetting composition. Examples of suitable surfactants include, but are not limited to, the surfactants described in JP-A-62-36663, JP-A-61-226746, JP-A-61-226745, JP-A-62-170950, JP-A-63-34540, JP-A-7-230165, JP-A-8-62834, JP-A-9-54432 and JP-A-9-5988.

Examples of suitable non-ionic surfactants include, but are not limited to, polyoxyethylene alkyl ethers such as polyoxyethylene lauryl ether, polyoxyethylene stearyl ether, polyoxyethylene cetyl ether and polyoxyethylene oleyl ether, polyoxyethylene alkyl allyl ethers such as polyoxyethylene octyl phenol ether and polyoxyethylene nonyl phenol ether, polyoxyethylene-polyoxypropylene block copolymers, sorbitol fatty acid esters such as sorbitol monolaurate, sorbitol monopalmitate, sorbitol monostearate, sorbitol monooleate, sorbitol trioleate and sorbitol tristearate, and polyoxyethylene sorbitol fatty acid esters such as polyoxyethylene sorbitol monolaurate, polyoxyethylene sorbitol monopalmitate, polyoxyethylene sorbitol monostearate, polyoxyethylene sorbitol trioleate and polyoxyethylene sorbitol tristearate.

Commercially available fluorine containing or silicon containing surfactants include, but are not limited to, Eftop EF301, EF303 (produced by Shin-Akita Kasei K.K.), Megafac F171, F173, F176, F189, R08 (produced by Dainippon Ink & Chemicals Inc.), Surflon S-382, SC101, 102, 103, 104, 105, 106 (produced by Asahi Glass Co., Ltd.) and Troysol S-366 (produced by Troy Chemical K.K.). Polysiloxane polymer KP-341 (produced by Shin-Etsu Chemical Co., Ltd.) can also be used as the silicon-containing surfactant.

In some embodiments, the thermosetting composition can optionally contain at least one plasticizer. The concentration of the optional plasticizer, if employed, can range from about 1 wt % to about 10 wt % of total weight of the thermosetting composition. A preferred amount of plasticizer can be from about 2 wt % to about 10 wt %.

In general, the plasticizer should have a lower volatility than the solvent employed at the typical bake temperatures of about 70° C. to about 150° C., so that it remains in the film after the first baking step. This typically means that the plasticizer of this invention has a higher boiling point than the solvent employed, unless interaction of the functional groups of the plasticizer with other components of the thermosetting composition decreases its volatility sufficiently. Examples of plasticizers include, but are not limited to, ethylene glycol, diethylene glycol, polyethylene glycol, propylene glycol, tripropylene glycol, polypropylene glycol, glycerol, butanediol, hexanediol, sorbitol, cyclohexanediol, 4,8-bis(hydroxymethyl)-tricyclo(5.2.1.0,2,6)decane and a 2-oxepanone co-polymer with 2-ethyl-2-(hydroxymethyl)-1,3-propanediol. Preferred polyhydroxy compounds with at least two hydroxyl groups are diethylene glycol, tripropylene glycol, and a 2-oxepanone co-polymer with 2-ethyl-2-(hydroxymethyl)-1,3-propanediol. Preferred saturated glycol mono ethers are saturated mono ethers of tripropylene glycol, triethylene glycol and tetraethylene glycol.

Although other reactions may be taking place, and not wishing to be bound by theory, it is thought that the thermal curing of the polyimide described herein can take place by the mechanism illustrated in Scheme 1.

Scheme 1

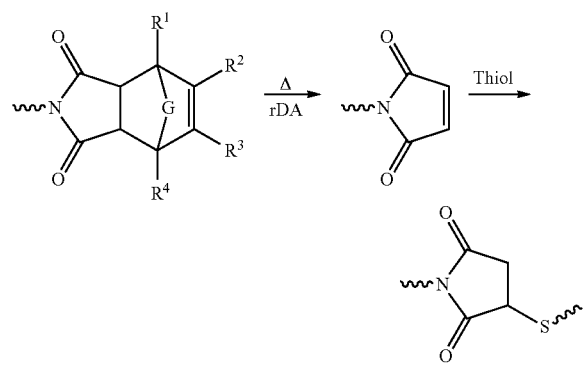

The polyimide described herein, a required ingredient of the thermosetting composition, possesses end groups that are "masked" maleimide groups. Maleimides can react rapidly with thiols under ambient conditions in solution through addition reactions of the SH group across the maleimide C=C double bond. A key aspect of the present disclosure is that the polyimides described herein contain polymer end groups that are not free maleimides, but function as latent or "masked" maleimides, in order to maintain solution stability over the course of the product shelf life. Upon heating to a sufficient temperature (e.g., at most about 250° C.), the polymer end groups undergo a cycloreversion (e.g. a Retro-Diels-Alder (rDA)) reaction to unmask the maleimide group, which is now reactive to a thiol group. Since the thiol-maleimide reaction in the film (i.e., a solid state) is slower than in solution, the optional non-nucleophilic basic additive can be added to assist in lowering the temperature necessary for curing to form an insoluble, cross-linked material.

In general, in order to minimize film shrinkage during the cure, the compound(s) or compounds formed via the cycloreversion reaction should either represent a small percentage of the total film mass or the compounds should become an integral part of the final baked film through other thermal reactions. If this moiety does not become an integral part of the final baked film, it should be volatile and completely leave the film during the final bake step. This is to insure that there is no leaching of the released moiety from the final baked film over time.

The present disclosure is also directed to a manufacturing process for producing a thermoset coating. In some embodiments, the process includes
 a) coating a substrate with a thermosetting composition of the present disclosure to form a coated substrate, and
 b) baking the coated substrate (e.g., at a temperature or temperatures for a period of time) to cure the thermosetting composition.

In another embodiment, the present disclosure is also directed to a manufacturing process for producing a thermoset coating that includes:
 a) providing a substrate,
 b) coating a substrate with a thermosetting composition of the present disclosure to form a coated substrate,
 c) baking the coated substrate in a first baking step at a temperature $T_1$ to remove most of the solvent, and
 d) baking the coated substrate in a second baking step at a temperature $T_2$ to cure the coating (e.g., render the coating insoluble in an organic solvent), where $T_1 \leq 150°$ C., $180°$ C.$\leq T_2 \leq 250°$ C. and where the total film thickness loss from step c to step d is <10%.

The substrate can be, for example, a semiconductor material such as a silicon wafer, a compound semiconductor (Groups III-V) or (Groups II-VI) wafer, a ceramic, a glass or quartz substrate. The substrate can also contain films or structures used for electronic circuit fabrication such as organic or inorganic dielectrics, or copper or other wiring metals.

The manufacturing process may optionally include the step of pre-wetting a substrate with a solvent. Any suitable method of treatment of the substrate with a solvent known to those skilled in the art may be employed. Examples include treatment of the substrate with solvent by spraying, streaming or immersing the substrate into the solvent. The time and temperature of treatment will depend on the particular substrate and method, which may employ elevated temperatures. Any suitable solvent or solvent blend may be employed. Preferred solvents are those used in the thermosetting composition of the present disclosure.

The process may optionally include the step of pre-coating a substrate with a solution containing an adhesion promoter. Any suitable method of treatment of the substrate with adhesion promoter known to those skilled in the art may be employed. Examples include treatment of the substrate with adhesion promoter vapors, solutions or at 100% concentration. The time and temperature of treatment will depend on the particular substrate, adhesion promoter, and method, which may employ elevated temperatures. Any suitable external adhesion promoter may be employed. Classes of suitable external adhesion promoters include, but are not limited to, vinylalkoxysilanes, methacryloxy-alkoxyysilanes, mercaptoalkoxysilanes, aminoalkoxysilanes, epoxyalkoxysilanes and glycidoxyalkoxysilanes.

In some embodiments, a thermosetting composition of this disclosure is coated on a suitable substrate to form an unbaked coated substrate. Coating methods for the thermosetting composition include, but are not limited to, spray coating, spin coating, offset printing, ink jet printing, roller coating, screen printing, extrusion coating, meniscus coating, curtain coating, and immersion coating. Other techniques that direct discrete units of fluid or continuous jets, or continuous sheets of fluid to a surface can also be used. The parameters for coating will depend on the particular coating tool, and are known to those skilled in the art.

In a preferred embodiment, the thermosetting composition can be deposited onto a substrate surface using a variety of low viscosity deposition tools. A low viscosity deposition tool is a device that deposits a dilute solution onto a surface by ejecting the solution through an orifice toward the surface without the tool being in direct contact with the surface. A preferred direct-write deposition tool is an inkjet device, e.g., a piezo-electric, thermal, drop-on-demand or continuous ink jet device. Other examples of direct-write deposition tools include aerosol jets and automated syringes, such as the MICROPEN tool available from Ohmcraft, Inc. (Honeoye Falls, N.Y.).

Regardless of the coating method employed, after the thermosetting composition is coated to a substrate, the unbaked coated substrate is typically heated at an elevated temperature using a baking means. Any suitable baking means may be employed. Examples of suitable baking means include, but are not limited to, hot plates, infrared lamps, convection ovens, and thermal heating elements on ink jet printing heads.

In one embodiment, the unbaked coated substrate is baked using the baking means at a suitable temperature in a one-step process. In such embodiments, the baking temperature can range from approximately 180° C. to approximately 250° C. and produce a substrate coated with a cured thermoset film. The time may vary depending on the baking means and the temperature employed. For example, when a convection oven is employed as the baking means, the time may range from approximately 10 minutes to approximately 120 minutes. When a hot plate is employed, the time may vary from approximately 1 minute to about 60 minutes. In some embodiments, the temperature may range from approximately 200° C. to approximately 250° C. Those skilled in the art can determine with routine experimentation the suitable times and temperatures, which will depend on the particular solvent, thiol, endcap groups, and additives employed in the thermosetting composition and the particular baking means employed.

In another embodiment, the temperature of the baking means may be ramped. Suitable starting temperatures may range from about 80° C. to about 180° C. and ramp to a final temperature from about approximately 180° C. to approximately 250° C. to produce a substrate coated with a cured thermoset film. Those skilled in the art can determine with routine experimentation the suitable starting and ending temperatures and ramp times, which will depend on the particular solvent, thiol, endcap groups, and additives employed in the thermosetting composition and the particular baking means employed.

In another embodiment, the unbaked coated substrate may be baked in a two-step process. The unbaked coated substrate can be baked in a first baking step at a temperature between approximately 70° C. to about 150° C. for a time dependent on the chosen baking means to produce a dried, uncured coated substrate. Preferably, the first baking temperature range is from about 80° C. to about 140° C. (e.g., from about 100° C. to about 140° C. or from about 100° C. to about 130° C.). The purpose of the first baking step is to primarily evaporate the residual solvent from the film of the coated substrate without inducing the cycloreversion reaction. The first baking step may employ a heating element on an ink jet print head.

The dried, uncured coated substrate can then be baked in a second baking step at approximately 180° C. to approximately 250° C., preferably at approximately 200° C. to approximately 250° C., to produce a substrate coated with a cured thermoset film. Those skilled in the art can determine with routine experimentation suitable times and temperatures, which will depend on the particular solvent, thiol, endcap, and additives employed in the composition and the particular baking means employed.

The purpose of this second bake step is thought to (1) cause the cycloreversion reaction on the polymer end groups to generate maleimide end groups and (2) cause the crosslinking reaction between the maleimide end groups on the polymer and the multifunctional thiol compound.

The crosslinked polyimide film obtained from these process embodiments is an insulating film with excellent heat and chemical resistance and electrical insulating properties.

In some embodiments, this disclosure features an article formed by a process described herein. Examples of such articles include a semiconductor substrate, a flexible film for electronics, a wire isolation, a wire coating, a wire enamel, or an inked substrate. In some embodiments, this disclosure features a semiconductor device containing the article described above. For example, the semiconductor device can be an integrated circuit, a light emitting diode, a solar cell, and a transistor.

In one embodiment, the present disclosure is directed to a process for producing a free-standing film of the thermoset compositions described herein. The process can include the following steps:
  a) coating a substrate with a thermosetting composition of the present disclosure to form a film coated substrate,
  b) baking the film coated substrate (e.g., in a first baking step at a temperature $T_1$) to remove at least a portion (e.g., substantially all) of the solvent in the thermosetting composition; and
  c) releasing the film coating from the substrate (e.g., by applying a mechanical force or a chemical treatment) to obtain a free-standing film.

In some embodiments, $T_1$ can be less than about 150° C. Examples of suitable substrates that can be used in the above process include, but not limited to, semiconductor materials such as a silicon oxide wafer (which can facilitate release of the film by using a HF treatment) and various plastic carriers such as polyethylene terephthalate (PET) substrates (which is flexible and can be easily removed by peeling).

Optionally, additional treatment of the film, such as exposure to radiation, corona, plasma and/or microwave radiation or a second baking step at a temperature $T_2$ (e.g., from about 180° C. to about 250° C.) can be applied to cure the film coating after the first baking step and before releasing the film to become free-standing.

Optionally, additional treatments that can be applied to the free-standing film include, but not limited to, washing the free-standing film with water or solvent and/or drying the free-standing film.

An example of the mechanical force to remove the film includes, but not limited to, peeling. An example of a chemical treatment to release the film includes, but not limited to, a dilute aqueous HF solution treatment.

In some embodiments, once the free-standing film is formed, it can be applied to a semiconductor substrate suitable for use in semiconductor devices. Examples of such semiconductor substrates include printed circuit boards and flexible printed circuit boards.

The contents of all publications cited herein (e.g., patents, patent application publications, and articles) are hereby incorporated by reference in their entirety.

The following examples are provided to illustrate the principles and practice of the present invention more clearly. It should be understood that the present invention is not limited to the examples described.

Synthesis Example 1

Synthesis of Polyimide PI-1

The polymerization reaction was performed in a one liter three-neck, jacketed round bottomed flask equipped with a mechanical agitator, a thermocouple and a nitrogen inlet to keep positive nitrogen pressure throughout the reaction. The flask was charged with 39.95 grams of 4,4'-[1,4-phenylene-bis(1-methylethylidene)] bisaniline (DAPI) and 600 g of anhydrous NMP. The contents were agitated until a homogeneous solution was obtained at 18-20° C. Next, 61.08 grams of hexafluoroisopropylidenediphthalic anhydride (6-FDA) was charged through a funnel to the stirring diamine solution. The 6-FDA charging funnel was rinsed into the reaction flask with 66.0 grams of anhydrous NMP. The mixture was warmed to 60° C. and agitated for 3 hours.

To perform the endcapping reaction, 4.2 grams of exo-3,6-epoxy-1,2,3,6-tetrahydrophthalic anhydride (OxoNadic Anhydride) and 2.0 grams of pyridine were charged to flask. The mixture was agitated at 60° C. for 3 hours.

To perform the imidization reaction, 10.2 grams of acetic anhydride and 2.0 grams of pyridine were charged to reaction vessel. The reaction mixture was warmed to 100° C. and the agitation was continued for 12 hours. A small sample (1 g) was withdrawn and precipitated into 50:50 methanol:water (10 ml). The solid was isolated by filtration and dried. FTIR analysis showed that the imidization reaction was complete.

The solution was cooled to room temperature added dropwise into 4 liters of vigorously stirred de-ionized water to precipitate the polymer. The polymer was collected by filtration and washed with one liter of de-ionized water. The filter cake was re-slurried with one liter of methanol and filtered. The wet filter cake was dried in air for 12 hours and then the polymer was dried under vacuum at 70° C. for 12 hours. The polymer was characterized by GPC for molecular weight, by $^1$H NMR for composition, FTIR for absence of amide and anhydride peaks, by Karl Fisher titration for water and by GC for residual solvent.

Synthesis Example 2

Synthesis of Polyimide PI-2

The procedure in Synthesis Example 1 was employed except that the reagent amounts used were as follows: 39.95 grams of 4,4'-[1,4-phenylene-bis(1-methylethylidene)] bisaniline (DAPI). 300 grams of anhydrous NMP, 61.08 grams of hexafluoroisopropylidenediphthalic anhydride (6-FDA), 33.0 grams of anhydrous NMP, 4.2 grams of exo-3,6-epoxy-1,2,3,6-tetrahydrophthalic anhydride, 2.0 grams of pyridine, 10.2 grams of acetic anhydride, and 2.0 grams of pyridine.

Synthesis Examples 3-5

Synthesis of Polyimides PI-3, PI-4, and PI-5

Polyimides PI-3, PI-4, and PI-5 were synthesized according to the procedure in Synthesis Example 1 except for any variations noted in Table 1. ODA in PI-5 is oxydianiline.

TABLE 1

| Synthesis Example | Polymer ID# | Diamine:Dianhydride (mole ratio) | Reaction Conc. (wt %) | Mw | Mw/Mn |
|---|---|---|---|---|---|
| SE-1 | PI-1 | DAPI:6FDA (12:11) | 15 | 13500 | 2.86 |
| SE-2 | PI-2 | DAPI:6FDA (12:11) | 30 | 19300 | 3.42 |
| SE-3 | PI-3 | DAPI:6FDA (6:5) | 15 | 9330 | 2.4 |
| SE-4 | PI-4 | DAPI:6FDA (8:7) | 15 | 11500 | 2.9 |
| SE-5 | PI-5 | DAPI:ODA:6FDA (6:6:11) | 15 | 13600 | 3 |

Synthesis Examples 6-12 and Comparative Synthesis Example 1

Synthesis of Polyimide Polymers PPI-6 Through PPI-12 and (Comparative) Polyimide Polymer CPI-1

The polymers are prepared according to Synthesis Example 1 with variations noted in Table 2. Tables 3-5 contain the chemical structures of the reactants for these examples.

TABLE 2

| Synthesis Example | Polymer # | Diamine | Dianhydride | Diamine:Dianhydride (mole ratio) | Reaction Conc. (wt %) | Monoanhydride | Mw | Mw/Mn |
|---|---|---|---|---|---|---|---|---|
| SE-6 | PPI-6 | Diamine 1 | Dianhydride 2 | 8:7 | 15 | Monoanhydride 2 | 16,000 | 2.9 |
| SE-7 | PPI-7 | Diamine 2 | Dianhydride 2 | 6:5 | 15 | Monoanhydride 2 | 22,000 | 3.2 |
| SE-8 | PPI-8 | Diamine 3 | Dianhydride 2 | 12:11 | 15 | Monoanhydride 1 | 18,100 | 2.8 |

TABLE 2-continued

| Synthesis Example | Polymer # | Diamine | Dianhydride | Diamine: Dianhydride (mole ratio) | Reaction Conc. (wt %) | Monoanhydride | Mw | Mw/Mn |
|---|---|---|---|---|---|---|---|---|
| SE-9 | PPI-9 | Diamine 1 | Dianhydride 3 | 6:5 | 15 | Monoanhydride 4 | 13600 | 3.1 |
| SE-10 | PPI-10 | Diamine 2 | Dianhydride 3 | 8:7 | 13 | Monoanhydride 1 | 16,100 | 2.8 |
| SE-11 | PPI-11 | Diamine 3 | Dianhydride 3 | 12:11 | 13 | Monoanhydride 4 | 15,600 | 3.2 |
| SE-12 | PPI-12 | Diamine 4 | Dianhydride 2 | 12:11 | 13 | Monoanhydride 1 | 13400 | 2.9 |
| CSE-1 | CPI-1 | Diamine 4 | Dianhydride 1 | 12:11 | 15 | Monoanhydride 3 | 11500 | 2.6 |

TABLE 3

Diamines 1  4,4'-[1,4-phenylene-bis(1-methyl-ethylidene)]bisaniline    DAPI 2  5-(4-aminophenoxy)-3-[4-(4-aminophenoxy)phenyl]-1,1,3-trimethylindan    DAPI ether 3  6,6'-bis(4-aminophenoxy)-3,3,3',3'-tetramethyl-1,1'-spirobiindan    Spirobiindan 4  5,7-diamino-1,1-dimethylindan

TABLE 4

Dianhydrides

| | | | |
|---|---|---|---|
| 1 | hexafluoroisopropylidene)diphthalic Anhydride) | 6-FDA | |
| 2 | 1-(3',4'-dicarboxyphenyl)-1,3,3-trimethylindan-5,6-dicarboxylic acid dianhydride | DAPI dianhydride | |
| 3 | 5-(2,5-dioxotetrahydro)-3-methyl-3-cyclohexene-1,2-dicarboxylic anhydride | | |

TABLE 5

Monoanhydrides

| | | | |
|---|---|---|---|
| 1 | exo-3,6-epoxy-1,2,3,6-tetrahydrophthalic anhydride | oxonadic anhydride | |
| 2 | 8-Methyl-4,10-dioxatricyclo[5.2.1.0$^{2,6}$]dec-8-ene-3,5-dione | Methyl Oxonadic anhydride | |
| 3 | 1,2,3,6-tetrahydro-methyl-3,6-methanophthalic anhydride | Methyl Nadic anhydride | |

TABLE 5-continued

| | | Monoanhydrides | |
|---|---|---|---|
| 4 | 10-Isopropylidene-4-oxatricyclo[5.2.1.0²,⁶]dec-8-ene-3,5-dione | Isopropylidene Nadic anhydride | 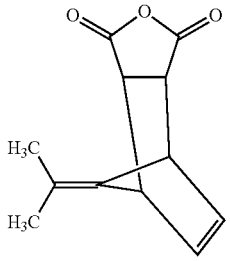 |

Formulation Examples FE-1 Through FE-16

Thermosetting composition components as described in the examples were mixed in an amber-bottle and a mixture of solvents added to adjust the solid content of solution and stirred until a homogeneous solution was obtained. The solution was filtered through a 1.0 μm filter into a clean amber-bottle. Tables 6 and 7 contain information concerning polythiols and adhesion promoters listed in the formulations in Table 8 (Formulation Examples FE-1 through FE-16) and also Table 11 (Formulation Examples FE17 through FE-23 and Comparative Formulation 1).

TABLE 6

| | | Polythiols |
|---|---|---|
| ID | Name | Structure |
| T-1 | Pentaerythritol Tetrakis(mercaptoacetate) | 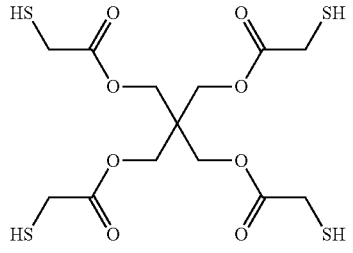 [SMILES: O=C(CS)OCC(COC(=O)CS)(COC(=O)CS)COC(=O)CS] |
| T-2 | Trimethylolpropane Tris(3-mercaptopropionate) | 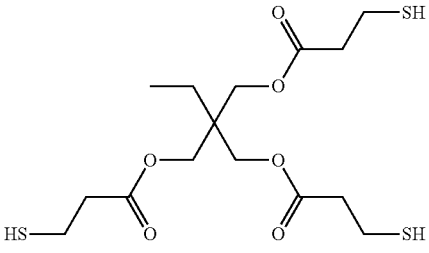 [SMILES: CCC(COC(=O)CCS)(COC(=O)CCS)COC(=O)CCS] |
| T-3 | Pentaerythritol Tetrakis(3-mercaptopropionate) | |
| T-4 | Dipentaerythritol Hexakis(3-mercaptopropionate) |  |

TABLE 6-continued

| | | Polythiols |
|---|---|---|
| ID | Name | Structure |
| T-5 | Ethoxylated Trimethylolpropane Tri-3-Mercaptopropionate Where (t1 + t2 + t3) = 7 | |
| T-6 | Ethoxylated Trimethylolpropane Tri-3-Mercaptopropionate Where (t1 + t2 + t3) = 20 | |
| T-7 | Polycaprolactone triol Tri-3-Mercaptopropionate Where (t4 + t5 + t6) ≥ 3 and t4, t5, t6 ≠ 0 | |
| PPT-1 | Trimethylolpropane Tris(4-sulfanylcyclohexanecarboxylate) | |
| PPT-2 | Trimethylolpropane Tris(4-sulfanylcyclohexanecarboxylate)methylol | |

TABLE 7
Adhesion Promoters
| ID# | Name | Chemical Structure |
|---|---|---|
| AP-1 | Silquest A-187 | 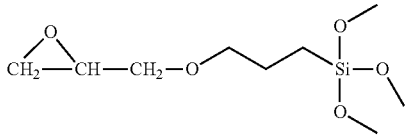 |
| AP-2 | (3-Triethoxysilylpropyl)ethyl carbamate (TESPEC) | 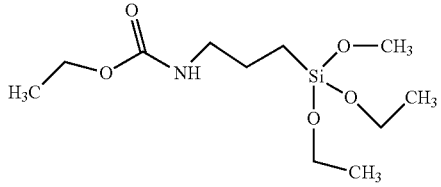 [SMILES: CCOC(=O)NCCC[Si](OC)(OCC)OCC] |
| AP-3 | Silquest A-1589 | 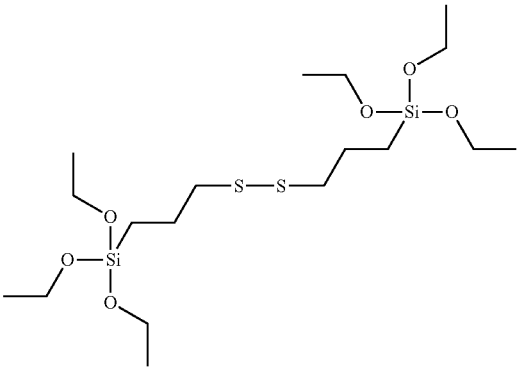 [SMILES: CCO[Si](CCCSSCCC[Si](OCC)(OCC)OCC)(OCC)OCC] |
| AP-4 | (3-Triethoxysilyl)propyl succinic anhydride | 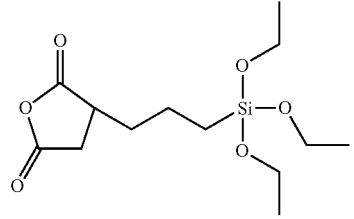 [SMILES: CCO[Si](CCCC1CC(=O)OC1=O)(OCC)OCC] |
| AP-5 | (3-Triethoxysilylpropyl)-t-butyl carbamate | 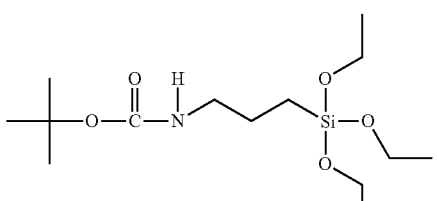 |
| AP-6 | (3-Glycidoxypropyl)triethoxysilane | 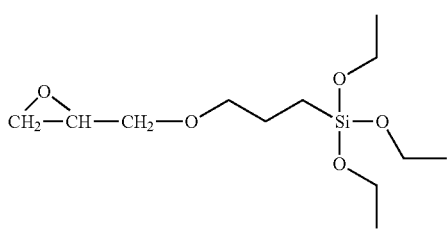 [SMILES: CCO[Si](CCCOCC1CO1)(OCC)OCC] |

TABLE 7-continued

| | Adhesion Promoters | |
|---|---|---|
| ID# | Name | Chemical Structure |
| AP-7 | (3-Glycidoxypropyl)Bis(trimethoxysiloxy)methylsilane | 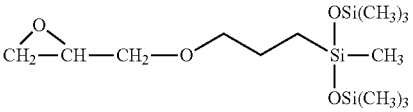 |
| AP-8 | 2-(3,4-epoxycyclohexyl)ethyltrimethoxysilane | 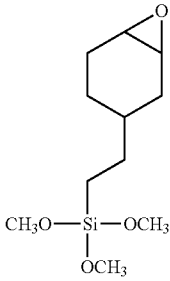 |

TABLE 8

Formulation Examples FE1-FE16

| Form. Ex. | Poly. | Polymer (wt %) | Adhesion Promoter ID | (wt %) | Polythiol ID | (wt %) | Catalyst ID | (wt %) | Solvent 1 | Solvent 2 |
|---|---|---|---|---|---|---|---|---|---|---|
| FE-1 | PI-1 | 35 | AP-1 | 3.5 | T-4 | 7.0 | DCMA | 0 | GBL | none |
| FE-2 | PI-1 | 35 | AP-1 | 3.5 | T-7 | 7.0 | DCMA | 0 | GBL | none |
| FE-3 | PI-1 | 35 | AP-1 | 3.5 | T-5 | 7.0 | DCMA | 0 | GBL | none |
| FE-4 | PI-1 | 35 | AP-1 | 3.5 | T-5 | 7.0 | TEA | 0.35 | GBL | none |
| FE-5 | PI-1 | 35 | AP-1 | 3.5 | T-5 | 7.0 | DBU | 0.35 | GBL | none |
| FE-6 | PI-1 | 35 | AP-1 | 3.5 | T-5 | 7.0 | DCMA | 0.35 | GBL | none |
| FE-7 | PI-1 | 35 | AP-1 | 3.5 | T-5 | 7.0 | DCMA | 0.35 | GBL | EL |
| FE-8 | PI-1 | 35 | AP-1 | 3.5 | T-5 | 7.0 | DCMA | 0.35 | PGMEA | PGME |
| FE-9 | PI-2 | 35 | AP-1 | 1.75 | T-5 | 7.0 | DCMA | 0.35 | GBL | none |
| FE-10 | PI-2 | 35 | AP-1 | 3.5 | T-5 | 7.0 | DCMA | 0.35 | GBL | none |
| FE-11 | PI-2 | 35 | AP-1 | 5.25 | T-5 | 7.0 | DCMA | 0.35 | GBL | none |
| FE-12 | PI-2 | 35 | AP-1 | 3.5 | T-5 | 3.5 | DCMA | 0.35 | GBL | none |
| FE-13 | PI-2 | 35 | AP-1 | 3.5 | T-5 | 0.53 | DCMA | 0.35 | GBL | none |
| FE-14 | PI-2 | 35 | AP-1 | 3.5 | T-5 | 8.75 | DCMA | 0.35 | GBL | none |
| FE-15 | PI-5 | 35 | AP-1 | 3.5 | T-5 | 7.0 | DCMA | 0.35 | GBL | none |
| FE-16 | PI-2 | 35 | AP-1 | 3.5 | T-6 | 8.75 | DCMA | 0.35 | GBL | none |

Examples 1-9

Preparation of Coated Substrates with Cured Thermoset Coating

A thermosetting composition prepared above was spin coated on either a silicon or silicon dioxide wafer to form a coating with a thickness from about 5 to about 30 microns. The coated wafer was baked at 120° C. for 3 minutes. Coating defects and film cracking were checked by optical microscope. The film was heated under $N_2$ atmosphere in a convection oven at 200° C. for 1 hour. The resulting film was checked by optical microscope for film defects. The film was immersed in various solvents (PGMEA, GBL, acetone and other) to test preliminary solvent resistance. When a silicon dioxide wafer was used as substrate the film was released from the wafer by treatment with 50:1 water:HF solution. The released film was dried in under $N_2$ in a dry box for 24 hours. The dried film was used for mechanical testing by TMA and DMA (modulus, elongation to break, Tg and CTE). Coating, baking, and other details are reported in Table 9 and the mechanical properties are reported in Table 10. As noted in Table 9, cured films of FE-6, FE-14, and FE-15 were insoluble in the test solvents.

TABLE 9

Coated Substrates with Cured Thermoset Coating

| Example | Form. Ex. | SBFT (microns) | Film Quality | Cured FT (microns) | Cured Film Loss | Cured Film Quality | Solvent Test of Cured Film | | |
|---|---|---|---|---|---|---|---|---|---|
| | | | | | | | Acetone | GBL | PGMEA |
| 1 | FE-6 | 10.18 | Good | 9.80 | 3.70% | Good | INS | — | — |
| 2 | FE-6 | 10.20 | Good | 9.83 | 3.70% | Good | — | INS | — |
| 3 | FE-6 | 10.25 | Good | 9.88 | 3.60% | Good | — | — | INS |
| 4 | FE-14 | 9.69 | Good | 9.42 | 2.80% | Good | INS | — | — |
| 5 | FE-14 | 9.79 | Good | 9.53 | 2.60% | Good | — | INS | — |
| 6 | FE-14 | 9.89 | Good | 9.58 | 3.10% | Good | — | — | INS |
| 7 | FE-15 | 9.87 | Good | 9.41 | 4.70% | Good | INS | — | — |
| 8 | FE-15 | 9.85 | Good | 9.39 | 4.70% | Good | — | INS | — |
| 9 | FE-15 | 9.92 | Good | 9.46 | 4.60% | Good | — | — | INS |

SBFT = soft bake film thickness
FT = film thickness
INS = insoluble

TABLE 10

Mechanical Properties of Formulation Examples FE-14 and FE-15

| Cured Film Property | FE-14 Film | FE-15 Film |
|---|---|---|
| Tg, ° C. (TMA) | 217 | 220 |
| CTE, ppm/° C. | 96 | 99 |
| UTS, MPa | 96 | 95 |
| Elongation | 25-32% | 43-45% |
| Modulus, GPa | 2.75 | 2.7 |

Formulation Examples FE-17 Through FE-23 and Comparative Formulation Example 1

Formulation Examples FE-17 through FE-23 and Comparative Formulation Example 1 are prepared according to the procedure described for Formulation Example 1 with the details shown in Table 11.

TABLE 11

Formulation Examples FE-17 through FE-23 and Comparative Formulation 1

| Form. Ex | Polymer (conc. wt %) | Adhesion Promoter (conc. wt %) | Thiol (conc. wt %) | Catalyst (conc. wt %) | Solvent 1 | Solvent 2 |
|---|---|---|---|---|---|---|
| FE-17 | PPI-7 35 | AP-2 3.5 | T-5 8.75 | DCMA 0.35 | CP | EL |
| FE-18 | PPI-9 35 | AP-3 3.5 | T-5 8.75 | DCMA 0.35 | GBL | PGME |
| FE-19 | PPI-10 35 | AP-6 3.5 | T-6 8.75 | DBU 0.35 | CH | EL |
| FE-20 | PPI-11 35 | AP-7 3.5 | T-4 8.75 | THA 0.35 | DMI | PGME |
| CFE-1 | CPI-1 35 | AP-2 3.5 | PPT-1 7 | DCMA 0.35 | 2-H | EL |
| FE-21 | PPI-12 35 | AP-7 3.5 | PPT-2 8.75 | DCMA 0.35 | CP | MMB |
| FE-22 | PPI-6 35 | AP-1 3.5 | T-4 8.75 | DCMA 0.35 | CP | EL |
| FE-23 | PPI-8 35 | AP-2 3.5 | T-5 8.75 | DCMA 0.35 | GBL | PGME |

EL = ethyl lactate;
PGME = propylene glycol monomethyl ether;
CP = cyclopentanone;
GBL = gamma butyrolactone;
CH = cyclohexanone
MMB = 3-methyl-3-methoxybutanol;
HP = 2-heptanone;
DMIS = 2,5-dimethylisosorbide
DBU = diazabicycloundecene;
DCMA = dicyclohexylamine;
THA = trihexylamine

Examples 10-16 and Comparative Example 1

Formulations FE-17 through FE-23 are coated onto silicon wafers and are baked similarly to Examples 1-9 to give comparable results. CFE-1 is also coated and baked similar, but when immersed into solvent, is completely removed from the wafer.

Ink Jet Coating of Substrates with Cured Thermoset Coating

Thermosetting compositions shown in Table 12 below (2 mL) were transferred via syringe to an ink cartridge installed in a Dimatix DMP-2800 printer. The composition was dispensed at piezoelectric frequencies from 1-20 KHz at the indicated temperatures. As shown in Table 13, for Examples 17 and 18, uniformity of droplet size was found to be excellent and there was no clogging of the inkjet nozzles when printing was resumed after ceasing operation for 4, 24 and 72 hour periods. In contrast, Comparative Example 2 showed poor jetting initially and after 4 and 24 hours, and no jetting after storage for 72 hours.

TABLE 12

Formulation Examples FE-24, FE-25, and Comparative Formulation 2

| Form. Ex | Polymer (conc. wt %) | Adhesion Promoter (conc. wt %) | Thiol (conc. wt %) | Catalyst (conc. wt %) | Surfactant conc. (wt %) | Solvent |
|---|---|---|---|---|---|---|
| FE-24 | PI-2 7.5 | AP-1 0.83 | T-5 1.87 | DCMA 0.07 | PolyFox 0.00023 | GBL |
| FE-25 | PI-2 11.2 | AP-1 1.23 | T-5 2.8 | DCMA 0.11 | PolyFox 0.000336 | GBL |
| CFE-2 | PAA-1 4.5 | AP-2 0.03 | none | none | Troysol S366 0.045 | GBL |

PAA-1 is a polyamic acid derived from the reaction of 4,4'-oxydiphenylamine (ODA) and 4,4'-oxydiphthalic anhydride (ODPA) in GBL in a 0.96:1.00 ratio. An 18 wt % solution of this polymer has a kinematic viscosity that ranges from 3000-5000 cSt.

TABLE 13

Examples 17, 18, and Comparative Example 2

| Example | Form. Ex | T (° C.) | Frequency (KHz) | Drop Velocity (m/s) | Initial Observations | Storage Stability |
|---|---|---|---|---|---|---|
| 17 | FE-24 | 50 | 19-20 | 5-6 | Good drop formation | Excellent jetting after 4, 24, 72 h storage (15 of 16 nozzles) |
|  |  | 55 | 19-20 | 7-8 | Drops were formed but with long tails |  |
| 18 | FE-25 | 30 | 19-20 | 3-4 | Good drop formation | Excellent jetting after 4, 24, 72 h storage (14-16 of 16 nozzles) |
|  |  | 50 | 19-20 | 7-8 | Excellent drop formation |  |
| CE2 | CFE-26 | 30 | 1-2 | NA | Limited jetting (5 of 16 nozzles) | Limited jetting after 4 & 24 h storage (5 of 16 nozzles) No jetting after 72 h |
|  |  | 50 | 1-2 |  |  |  |

Comparative Synthesis Example CSE-2

Synthesis of Polyimides CPI-2 (Comparative Example)

Polyimides CPI-2 was synthesized according to the procedure in Synthesis Example 1 except the end-capping group was 1,2,3,6-tetrahydro-3,6-methanophthalic anhydride (nadic anhydride) instead of exo-3,6-epoxy-1,2,3,6-tetrahydrophthalic anhydride (oxo-nadic anhydride). The MW and PD were 14,116 Daltons and 4.0, respectively.

Comparative Synthesis Example CSE-3

Synthesis of Polyimide CPI-3 (Comparative Example)

Polyimide CPI-3 was synthesized according to the procedure in Synthesis Example 1 except the dianhydride was 4,4-Oxydiphthalic anhydride (ODPA) and the diamine was oxydianiline (ODA). After the imidization step, a large amount of precipitate was obtained. This illustrates the lower solubility that typical polyimides have in NMP relative to the polymers of the current disclosure.

Formulation Examples FE-26, FE-27 and Comparative Example CFE-3

Thermosetting composition components as described in Table 14 were mixed in an amber-bottle and a mixture of solvents added to adjust the solid content of solution and stirred until a homogeneous solution was obtained. The solution was filtered through a 1.0 μm filter into a clean amber-bottle. Table 14 contains information concerning these formulations.

TABLE 14

| Form. Ex. | Polymer Poly. | Polymer (wt %) | Adhesion Promoter ID | Adhesion Promoter (wt %) | Polythiol ID | Polythiol (wt %) | Catalyst ID | Catalyst (wt %) | Solvent 1 | Solvent 2 |
|---|---|---|---|---|---|---|---|---|---|---|
| FE-26 | PI-1 | 35 | None |  | T-6 | 7.0 | DCMA | 0.35 | GBL | none |
| FE-27 | PI-1 | 35 | AP-1 | 3.5 | T-6 | 7.0 | None |  | GBL | none |
| CFE-3 | CPI-2 | 35 | None |  | T-6 | 7.0 | DCMA | 0.35 | GBL | none |

Examples 19-21

Preparation of Coated Substrates with a Cured Thermoset Coating from FE-26

Thermosetting composition FE-26 prepared above was spin coated on a silicon wafer to form a coating with a thickness from about 5 to about 15 microns. The coated wafer was baked at 120° C. for 3 minutes. Coating defects and film cracking were checked by optical microscope. The film was heated under $N_2$ atmosphere in a convection oven at 200° C. for 1 hour. The resulting film was checked by optical microscope for film defects. The film was immersed in various solvents (PGMEA, GBL, acetone and other) to test preliminary solvent resistance. The results of these tests are shown in Table 15.

TABLE 15

| Example | Form. Ex. | SBFT (microns) | Film Quality | Cured FT (microns) | Cured Film Loss | Cured Film Quality | Solvent Rinse of Cured Film | | |
|---|---|---|---|---|---|---|---|---|---|
| | | | | | | | Acetone | GBL | PGMEA |
| 19 | FE-26 | 10.5 | Good | 9.87 | 6.00% | Good | INS | — | — |
| 20 | FE-26 | 10.5 | Good | 9.87 | 6.00% | Good | — | INS | — |
| 21 | FE-26 | 10.5 | Good | 9.87 | 6.00% | Good | — | — | INS |

INS = insoluble

Examples 22-24

Preparation of Coated Substrates with a Cured Thermoset Coating from, FE-27

These experiments were done exactly as described in Examples 19-21 except the thermosetting composition of FE-27 was used and the film was heated under $N_2$ atmosphere in a convection oven at 250° C. instead of 200° C. for 1 hour. The results of these tests are shown in Table 16.

TABLE 16

| Example | Form. Ex. | SBFT (microns) | Film Quality | Cured FT (microns) | Cured Film Loss | Cured Film Quality | Solvent Rinse of Cured Film | | |
|---|---|---|---|---|---|---|---|---|---|
| | | | | | | | Acetone | GBL | PGMEA |
| 22 | FE-27 | 10.80 | Good | 10.20 | 6.30% | Good | INS | — | — |
| 23 | FE-27 | 10.80 | Good | 10.20 | 6.30% | Good | — | INS | — |
| 24 | FE-27 | 10.80 | Good | 10.20 | 6.30% | Good | — | — | INS |

INS = insoluble

Comparative Examples CE-3- to CE-5

Preparation of Coated Substrates with a Cured Thermoset Coating from CFE-3

These experiments were done exactly as described in Examples 19-21 except the composition of CFE-3 was used. The results of these tests are shown in Table 17.

TABLE 17

| Example | Form. Ex. | SBFT (microns) | Film Quality | Cured FT (microns) | Cured Film Loss | Cured Film Quality | Solvent Rinse of Cured Film | | |
|---|---|---|---|---|---|---|---|---|---|
| | | | | | | | Acetone | GBL | PGMEA |
| CE-3 | CFE-3 | 8.56 | Good | 7.94 | 7.20% | Good | F* | — | — |
| CE-4 | CFE-3 | 8.56 | Good | 7.94 | 7.20% | Good | — | F** | — |
| CE-5 | CFE-3 | 8.56 | Good | 7.94 | 7.20% | Good | — | — | F** |

*The film was completely dissolved
**The film was not dissolved but extensive cracking was observed Solubility Example Tests of PI-1 (ST-1 to ST-5) and CPI-3 (CST-1 to CST-5)

9 g of a solvent (listed in Table 18) and 1 g of either Polymer PI-1 or Comparative Polymer CPI-3 were added to a small vial. Each vial was then agitated on a roller to assist in dissolving the polymer.

Vials containing Polymer PI-1 were completely dissolved in all tested solvents within 30 minutes. Additional 0.25 g increments of Polymer PI-1 were repeatedly added to the vial and rerolled for 30 minutes until the last portion was added. The final roll period was extended from 30 minutes to overnight. Table 18 contains information on the amount of Polymer PI-1 soluble in the solvent (ST-1 to ST-5).

Comparative Polymer CPI-3 was insoluble in all of the solvents at the 10% level (9 g solvent to 1 g polymer). 10 g of additional solvent was added to each of the 5 vials containing Comparative Polymer CPI-3 and the vial rolled overnight. After rolling overnight, a large portion of the Comparative Polymer CPI-3 remained undissolved indicating <5% solubility in the solvent. (See Table 18, CST-1 to CST-5).

This experiment shows that polymers of this disclosure have a great solubility advantage over a typical polyimide.

TABLE 18

| Experiment Number | Polymer | Solvent | Solubility |
|---|---|---|---|
| ST-1 | PI-1 | GBL | >28% |
| ST-2 | PI-1 | Cyclopentanone | >36% |
| ST-3 | PI-1 | Cyclohexanone | >25% |
| ST-4 | PI-1 | Acetone | >36% |
| ST-5 | PI-1 | PGMEA | >31% |
| CST-1 | CPI-3 | GBL | <5% |
| CST-2 | CPI-3 | Cyclopentanone | <5% |
| CST-3 | CPI-3 | Cyclohexanone | <5% |
| CST-4 | CPI-3 | Acetone | <5% |
| CST-5 | CPI-3 | PGMEA | <5% |

What is claimed is:

1. A polymer, comprising:
   a first repeat unit, the first repeat unit comprising at least one imide moiety and at least one indane-containing moiety; and
   at least one end-cap group at one end of the polymer, the end-cap group comprising a masked maleimide group and being capable of undergoing a cycloreversion reaction at a temperature of at most 250° C. in the solid state;
   wherein the masked maleimide group comprises a moiety of structure (IXa):

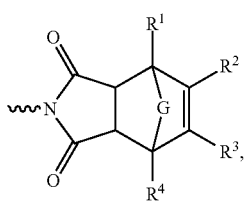

(IXa)

in which
   G is —O—, —(NR$^{100}$)—, —[C(R$^{101}$)=C(R$^{102}$)]—, or —[C=C(R$^{103}$)$_2$]—, where each of R$^{100}$, R$^{101}$, R$^{102}$ and R$^{103}$, independently, is H, an unsubstituted C$_1$-C$_{12}$ linear, branched, monocyclic or polycyclic alkyl group, or an unsubstituted phenyl group, and
   each of R$^1$, R$^2$, R$^3$ and R$^4$, independently, is H, an unsubstituted C$_1$-C$_{12}$ linear, branched, monocyclic or polycyclic alkyl group, an unsubstituted phenyl group, OR$^{104}$, CH$_2$OR$^{105}$, CH$_2$OC(=O)R$^{106}$, CH$_2$C(=O)OR$^{107}$, CH$_2$NHR$^{108}$, CH$_2$NHC(=O)R$^{109}$, CH$_2$C(=O)N(R$^{110}$)$_2$, C(=O)OR$^{111}$, where each of R$^{104}$, R$^{105}$, R$^{106}$, R$^{107}$, R$^{108}$, R$^{109}$, R$^{110}$, and R$^{111}$, independently, is H or an unsubstituted C$_1$-C$_6$ linear, branched, or monocyclic alkyl group.

2. The polymer of claim 1, wherein the indane-containing moiety comprises

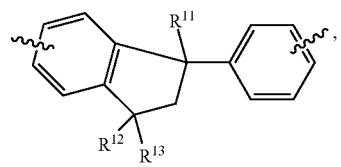

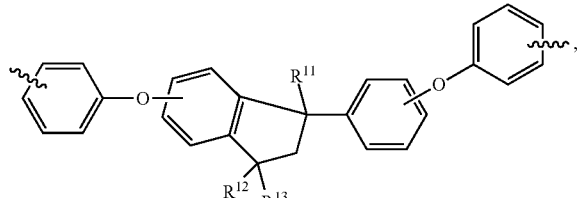

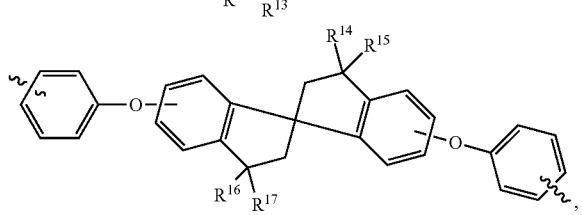

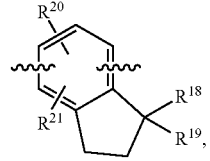

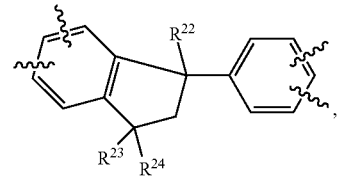

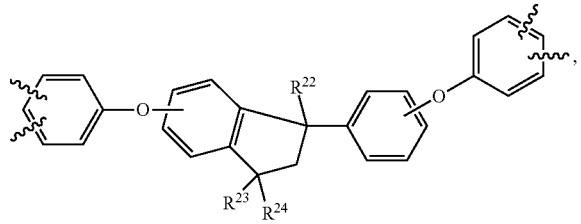

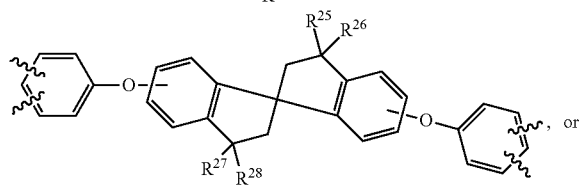

or

-continued

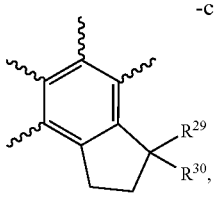

in which each of $R^{11}$-$R^{30}$, independently, is H or a substituted or unsubstituted $C_1$-$C_{10}$ linear or branched alkyl group.

3. The polymer of claim 2, wherein each of $R^{11}$-$R^{30}$, independently, is H or $CH_3$.

4. The polymer of claim 1, further comprising a second repeat unit different from the first repeat unit.

5. The polymer of claim 1, wherein the polymer is of structure I:

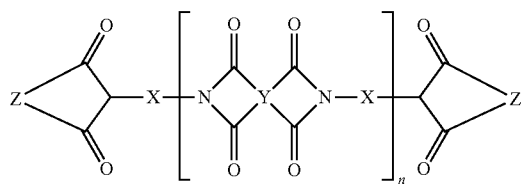

in which Z is a divalent organic group capable of undergoing a cycloreversion reaction, n is an integer greater than 5, each X, independently, is a divalent organic group, each Y, independently, is a tetravalent organic group, and at least one of X and Y comprises an indane-containing moiety.

6. The polymer of claim 1, wherein the polymer has a molecular weight of at least 1,000 g/mol.

7. A thermosetting composition, comprising:
the polymer of claim 1;
at least one multifunctional thiol compound, the thiol compound comprising at least two thiol groups;
at least one solvent; and
optionally, at least one non-nucleophilic basic additive.

8. The composition of claim 7, wherein the multifunctional thiol compound is of structure (VI):

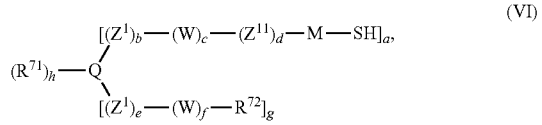

in which
a is an integer ranging from 2 to 10;
c is an integer ranging from 1 to 10;
each of b, d, and e, independently, is an integer ranging from 0 to 1;
each of f, g, and h, independently, is an integer ranging from 0 to 10;
Q is a multivalent organic nucleus;
each of $Z^1$, W, and $Z^{11}$, independently, is a divalent linking group;
each of $R^{71}$ and $R^{72}$, independently, is H, a substituted or unsubstituted, linear or branched $C_1$-$C_6$ alkyl group, or a substituted or unsubstituted $C_3$-$C_{10}$ cycloaliphatic group; and M is a substituted or unsubstituted $C_1$-$C_6$ linear or branched aliphatic group, a substituted or unsubstituted $C_3$-$C_{10}$ cycloaliphatic group, or a substituted or unsubstituted $C_6$-$C_{18}$ mononuclear or polynuclear aromatic group.

9. The composition of claim 8, further comprising the at least one non-nucleophilic basic additive.

10. The composition of claim 9, wherein the non-nucleophilic basic additive is a nitrogen-containing compound or a phosphorus-containing compound.

11. The composition of claim 7, wherein the polymer is from about 1 wt % to about 50 wt % of the composition.

12. The composition of claim 7, wherein the multifunctional thiol compound is from about 0.2 wt % to about 30 wt % of the composition.

13. The composition of claim 7, wherein the solvent is at least about 40 wt % of the composition.

14. A manufacturing process for producing a thermoset coating, comprising:
coating a substrate with the thermosetting composition of claim 7 form a coated substrate, and
baking the coated substrate to cure the thermosetting composition, thereby forming a thermoset coating on the substrate.

15. The process of claim 14, wherein coating the substrate comprises applying the thermosetting composition on the substrate by ink jet printing, spin coating, spray coating, dip coating, roller coating, or dynamic surface tension coating.

16. A device, comprising a coated substrate prepared by the manufacturing process of claim 14.

17. A manufacturing process for producing a free-standing film, comprising:
coating a substrate with the thermosetting composition of claim 7 to form a film coated substrate,
baking the film coated substrate to remove at least a portion of the at least one solvent, and
releasing the film coating from the substrate to obtain a free-standing film.

18. A free-standing film obtained by the manufacturing process of claim 17.

19. A polymer, comprising the condensation product of:
(a) at least one diamine;
(b) at least one dianhydride; and
(c) at least one monoanhydride comprising a masked maleic anhydride group;
wherein at least one of components (a) and (b) comprises an indane-containing moiety, the polymer comprises at least one end-cap group at one end, and the end-cap group comprises the masked maleic anhydride group and is capable of undergoing a cycloreversion reaction at a temperature of at most 250° C. in the solid state;
wherein the monoanhydride comprising the masked maleic anhydride is of structure (IX):

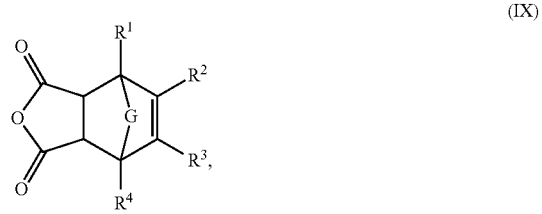

in which

G is —O—, —(NR$^{100}$)—, —[C(R$^{101}$)=C(R$^{102}$)]—, or —[C=C(R$^{103}$)$_2$]—, where each of R$^{100}$, R$^{101}$, R$^{102}$, and R$^{103}$, independently, is H, an unsubstituted C$_1$-C$_{12}$ linear, branched, monocyclic or polycyclic alkyl group, or an unsubstituted phenyl group, and each of R$^1$, R$^2$, R$^3$ and R$^4$, independently, is H, an unsubstituted C$_1$-C$_{12}$ linear, branched, monocyclic or polycyclic alkyl group, an unsubstituted phenyl group, OR$^{104}$, CH$_2$OR$^{105}$, CH$_2$OC(=O)R$^{106}$, CH$_2$C(=O)OR$^{107}$, CH$_2$NHR$^{108}$, CH$_2$NHC(=O)R$^{109}$, CH$_2$C(=O)N(R$^{110}$)$_2$, C(=O)OR$^1$, where each of R$^{104}$, R$^{105}$, R$^{106}$, R$^{107}$, R$^{108}$, R$^{109}$, R$^{110}$, and R$^{111}$, independently, is H or an unsubstituted C$_1$-C$_6$ linear, branched, or monocyclic alkyl group.

20. The polymer of claim 19, wherein the indane-containing moiety comprises

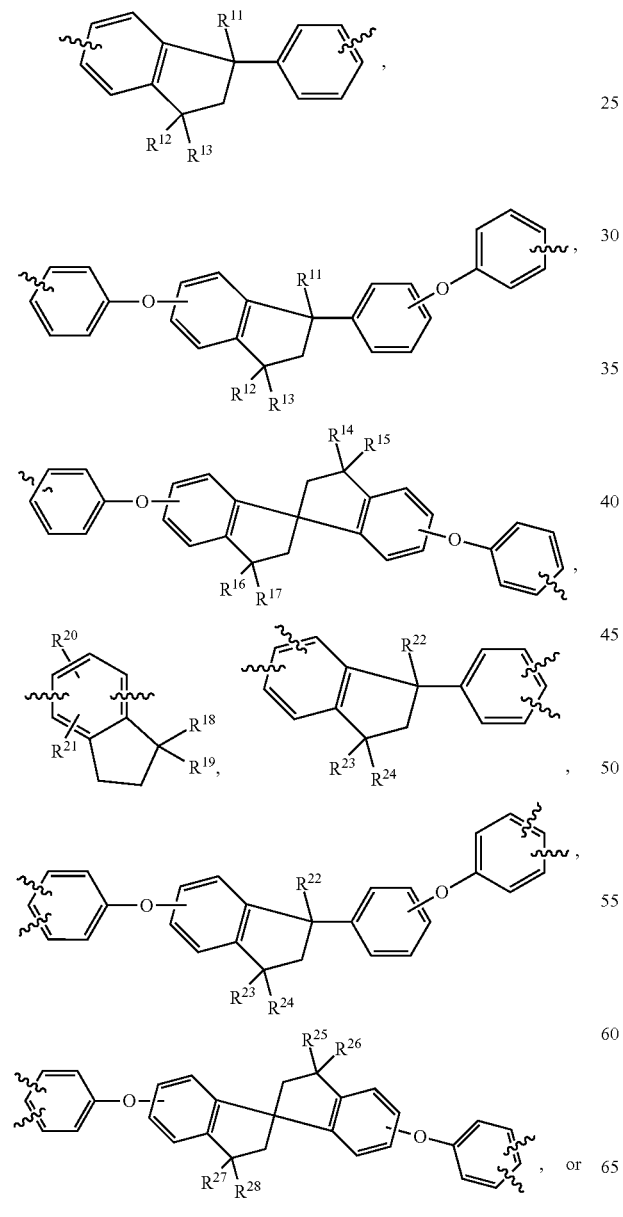

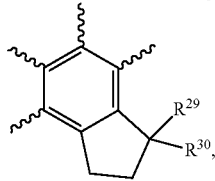

in which each of R$^{11}$-R$^{30}$, independently, is H or a substituted or unsubstituted C$_1$-C$_{10}$ linear or branched alkyl group.

21. The polymer of claim 20, wherein each of R$^{11}$-R$^{30}$, independently, is H or CH$_3$.

22. The polymer of claim 19, wherein the component comprising the indane-containing moiety is at least about 25 mole % of components (a) and (b).

23. A polymer, comprising:
a first repeat unit, the first repeat unit comprising at least one imide moiety and at least one indane-containing moiety; and
at least one end-cap group at one end of the polymer, the end-cap comprises a moiety of structure (IXa):

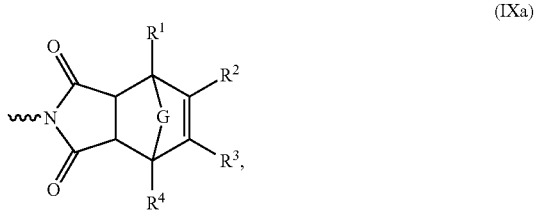

(IXa)

in which

G is —O—, —(NR$^{100}$)—, —[C(R$^{101}$)=C(R$^{102}$)]—, or —[C=C(R$^{103}$)$_2$]—, where each of R$^{100}$, R$^{101}$, R$^{102}$, and R$^{103}$, independently, is H, a substituted or unsubstituted C$_1$-C$_{12}$ linear, branched, monocyclic or polycyclic alkyl group, or a substituted or unsubstituted phenyl group, and each of R$^1$, R$^2$, R$^3$ and R$^4$, independently, is H, a substituted or unsubstituted C$_1$-C$_{12}$ linear, branched, monocyclic or polycyclic alkyl group, a substituted or unsubstituted phenyl group, OR$^{104}$, CH$_2$OR$^{105}$, CH$_2$OC(=O)R$^{106}$, CH$_2$C(=O)OR$^{107}$, CH$_2$NHR$^{108}$, CH$_2$NHC(=O)R$^{109}$, CH$_2$C(=O)N(R$^{110}$)$_2$, C(=O)OR$^{111}$, where each of R$^{104}$, R$^{105}$, R$^{106}$, R$^{107}$, R$^{108}$, R$^{109}$, R$^{110}$, and R$^{111}$, independently, is H or a substituted or unsubstituted C$_1$-C$_6$ linear, branched, or monocyclic alkyl group.

24. The polymer of claim 23, wherein

G is —O—, —(NR$^{100}$)—, —[C(R$^{101}$)=C(R$^{102}$)]—, or —[C=C(R$^{103}$)$_2$]—, where each of R$^{100}$, R$^{101}$, R$^{102}$, and R$^{103}$, independently, is H, an unsubstituted C$_1$-C$_{12}$ linear, branched, monocyclic or polycyclic alkyl group, or an unsubstituted phenyl group, and each of R$^1$, R$^2$, R$^3$ and R$^4$, independently, is H, an unsubstituted C$_1$-C$_{12}$ linear, branched, monocyclic or polycyclic alkyl group, an unsubstituted phenyl group, OR$^{104}$, CH$_2$OR$^{105}$, CH$_2$OC(=O)R$^{106}$, CH$_2$C(=O)OR$^{107}$, CH$_2$NHR$^{108}$, CH$_2$NHC(=O)R$^{109}$, CH$_2$C(=O)N(R$^{110}$)$_2$, C(=O)OR$^{111}$, where each of R$^{104}$, R$^{105}$, R$^{106}$, R$^{107}$, R$^{108}$, R$^{109}$, R$^{110}$, and R$^{111}$, independently, is H or an unsubstituted C$_1$-C$_6$ linear, branched, or monocyclic alkyl group.

25. The polymer of claim 23, wherein the indane-containing moiety comprises

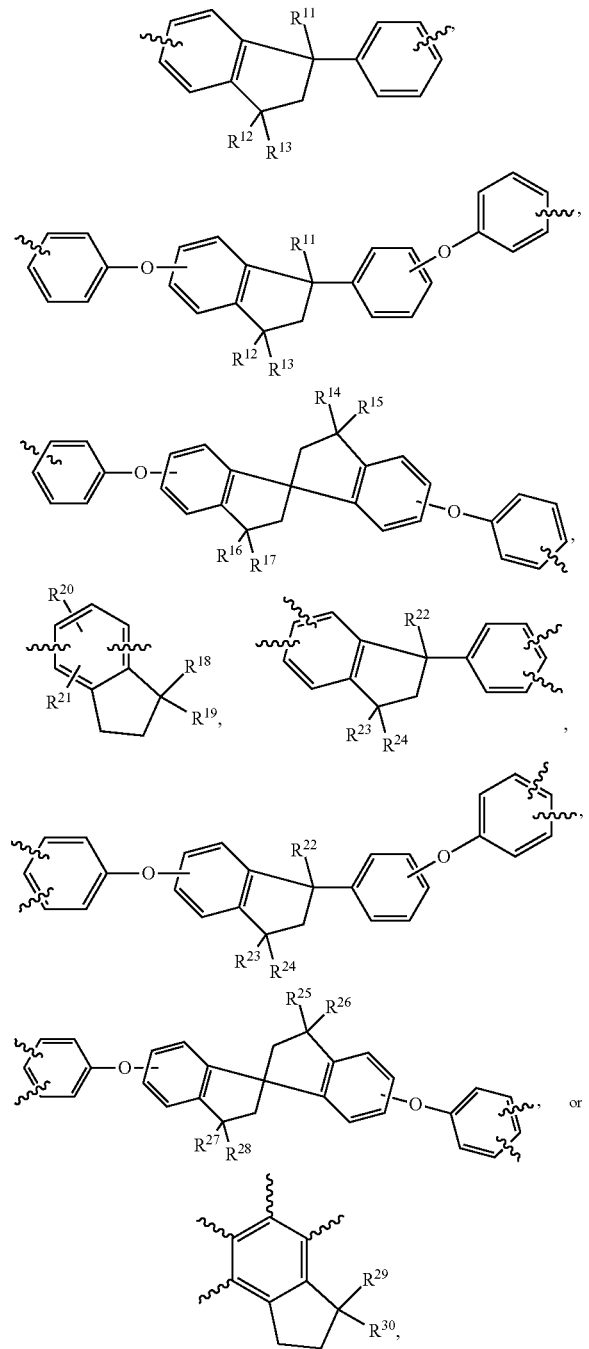

in which each of $R^{11}$-$R^{30}$, independently, is H or a substituted or unsubstituted $C_1$-$C_{10}$ linear or branched alkyl group.

26. The polymer of claim 25, wherein each of $R^{11}$-$R^{30}$, independently, is H or $CH_3$.

27. The polymer of claim 23, further comprising a second repeat unit different from the first repeat unit.

28. The polymer of claim 23 wherein the polymer is of structure I:

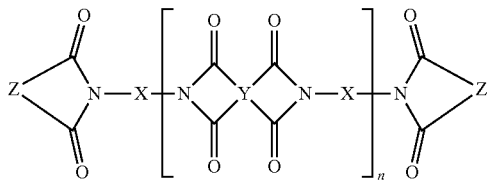

in which Z is a divalent organic group capable of undergoing a cycloreversion reaction, n is an integer greater than 5, each X, independently, is a divalent organic group, each Y, independently, is a tetravalent organic group, and at least one of X and Y comprises an indane-containing moiety.

29. The polymer of claim 23, wherein the polymer has a molecular weight of at least 1,000 g/mol.

30. A thermosetting composition, comprising:
the polymer of claim 23;
at least one multifunctional thiol compound, the thiol compound comprising at least two thiol groups;
at least one solvent; and
optionally, at least one non-nucleophilic basic additive.

31. The composition of claim 30, wherein the multifunctional thiol compound is of structure (VI):

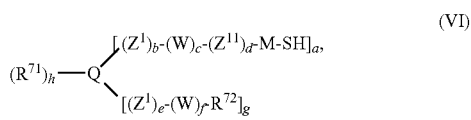

in which
a is an integer ranging from 2 to 10;
c is an integer ranging from 1 to 10;
each of b, d, and e, independently, is an integer ranging from 0 to 1;
each of f, g, and h, independently, is an integer ranging from 0 to 10;
Q is a multivalent organic nucleus;
each of $Z^1$, W, and $Z^{11}$, independently, is a divalent linking group;
each of $R^{71}$ and $R^{72}$, independently, is H, a substituted or unsubstituted, linear or branched $C_1$-$C_6$ alkyl group, or a substituted or unsubstituted $C_3$-$C_{10}$ cycloaliphatic group; and
M is a substituted or unsubstituted $C_1$-$C_6$ linear or branched aliphatic group, a substituted or unsubstituted $C_3$-$C_{10}$ cycloaliphatic group, or a substituted or unsubstituted $C_6$-$C_{18}$ mononuclear or polynuclear aromatic group.

32. The composition of claim 31, further comprising the at least one non-nucleophilic basic additive.

33. The composition of claim 32, wherein the non-nucleophilic basic additive is a nitrogen-containing compound or a phosphorus-containing compound.

34. The composition of claim 30, wherein the polymer is from about 1 wt % to about 50 wt % of the composition.

35. The composition of claim 30, wherein the multifunctional thiol compound is from about 0.2 wt % to about 30 wt % of the composition.

36. The composition of claim 30, wherein the solvent is at least about 40 wt % of the composition.

37. A manufacturing process for producing a thermoset coating, comprising:

coating a substrate with the thermosetting composition of claim 30 form a coated substrate, and baking the coated substrate to cure the thermosetting composition, thereby forming a thermoset coating on the substrate.

38. The process of claim 37, wherein coating the substrate comprises applying the thermosetting composition on the substrate by ink jet printing, spin coating, spray coating, dip coating, roller coating, or dynamic surface tension coating.

39. A manufacturing process for producing a free-standing film, comprising:

coating a substrate with the thermosetting composition of claim 30 to form a film coated substrate, baking the film coated substrate to remove at least a portion of the at least one solvent, and releasing the film coating from the substrate to obtain a free-standing film.

\* \* \* \* \*

UNITED STATES PATENT AND TRADEMARK OFFICE
CERTIFICATE OF CORRECTION

PATENT NO. : 10,604,628 B2
APPLICATION NO. : 15/608410
DATED : March 31, 2020
INVENTOR(S) : Sanjay Malik et al.

Page 1 of 1

It is certified that error appears in the above-identified patent and that said Letters Patent is hereby corrected as shown below:

In the Claims

Column 75

Lines 20-28, in Claim 5, delete " 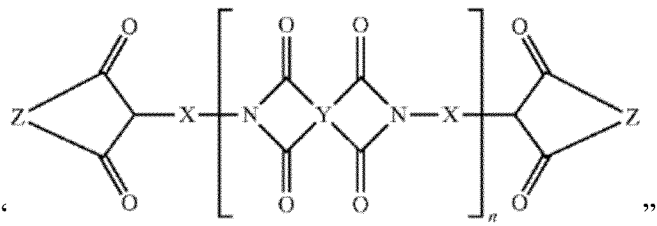 "

and insert -- 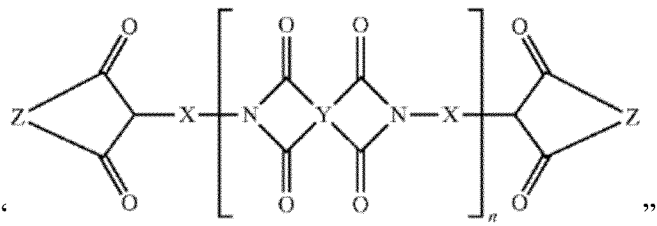 --

Column 76
Line 22, in Claim 14, delete "form" and insert -- to form --

Column 77
Line 13, in Claim 19, delete "C(=O)OR$^1$," and insert -- C(=O)OR$^{111}$, --

Column 81
Line 2, in Claim 37, delete "form" and insert -- to form --

Signed and Sealed this
Second Day of June, 2020

Andrei Iancu
*Director of the United States Patent and Trademark Office*